US009243243B2

(12) United States Patent
Hennemann et al.

(10) Patent No.: US 9,243,243 B2
(45) Date of Patent: Jan. 26, 2016

(54) MEANS AND METHODS FOR DETECTING PROTEIN-PEPTIDE INTERACTIONS

(75) Inventors: Hanjo Hennemann, Neuss (DE); Claudia Kruse, Bonn (DE); Sabine Hanke, Ruppichteroth-Winterscheid (DE); Annette Friebe, Burscheid (DE)

(73) Assignee: NEXIGEN GMBH, Cologne (DE)

( * ) Notice: Subject to any disclaimer, the term of this patent is extended or adjusted under 35 U.S.C. 154(b) by 1155 days.

(21) Appl. No.: 12/439,229

(22) PCT Filed: Aug. 31, 2007

(86) PCT No.: PCT/EP2007/007633
§ 371 (c)(1),
(2), (4) Date: Dec. 22, 2009

(87) PCT Pub. No.: WO2008/025564
PCT Pub. Date: Mar. 6, 2008

(65) Prior Publication Data
US 2010/0136535 A1 Jun. 3, 2010

(30) Foreign Application Priority Data

Aug. 31, 2006 (EP) .................................... 06018277
Aug. 16, 2007 (EP) .................................... 07016137

(51) Int. Cl.
*C12N 15/00* (2006.01)
*C12N 15/10* (2006.01)

(52) U.S. Cl.
CPC .................................. *C12N 15/1086* (2013.01)

(58) Field of Classification Search
None
See application file for complete search history.

(56) References Cited

U.S. PATENT DOCUMENTS

| 5,270,181 | A | 12/1993 | McCoy et al. |
| 5,283,173 | A | 2/1994 | Fields et al. |
| 5,776,689 | A | 7/1998 | Karin et al. |

FOREIGN PATENT DOCUMENTS

| WO | 95/31723 A1 | 11/1995 |
| WO | 9602561 A1 | 1/1996 |
| WO | 96/02561 A1 | 2/1996 |
| WO | 97/38127 | 10/1997 |
| WO | 98/49188 A1 | 11/1998 |
| WO | 00/05410 | 2/2000 |
| WO | 02/27020 A1 | 4/2002 |
| WO | 03/083136 A1 | 10/2003 |
| WO | 2004/074479 A1 | 9/2004 |
| WO | 2005/004798 | 8/2005 |
| WO | 2005/077099 A2 | 8/2005 |
| WO | 2005077105 A2 | 9/2006 |

OTHER PUBLICATIONS

Chalfie. Green fluorescent protein. Photochem Photobiol. Oct. 1995;62(4):651-6.*
Utsumi et al. In vitro synthesis of an N-myristoylated fusion protein that binds to the liposomal surface. Arch Biochem Biophys. Feb. 15, 1996;326(2):179-84.*
Song et al. Regulation of membrane and subunit interactions by N-myristoylation of a G protein alpha subunit in yeast. J Biol Chem. Aug. 23, 1996;271(34):20273-83.*
Ishitani et al. SOS3 function in plant salt tolerance requires N-myristoylation and calcium binding. Plant Cell. Sep. 2000;12(9):1667-78.*
Lui et al., "Combinatorial peptide library methods for immunogiology research," Experimental Hematology 31 (2003) pp. 11-30.
Smith et al., "Filamentous Fusion Phage: Novel Expression Vectors That Display Cloned Antigens on the Virion Surface," Science 228 (1985) pp. 1315-1317.
Arap et al., "Targeting the prostate for destruction through a vascular address," PNAS, vol. 99, No. 3 (2002) pp. 1527-1531.
Fields et al., "A novel genetic system to detect protein-protein interactions," Nature 340 (1989) pp. 245-246.
Petitjean et al., "Comparison of Thermosensitive Alleles of the CDC25 Gene Involved in the cAMP Metabolism of Saccharomyces cerevisiae," Genetics 124 (1990) pp. 797-806.
Evers et al., "Quantitative Understanding of the Energy Transfer between Fluorescent Proteins Connected via Flexible Peptide Linkers," Biochemistry 45 (2006) pp. 13183-13192.
Maeda et al., "Expression of a Bifunctional Chimeric Protein A-Vargula hilgendorfii Luciferase in Mammalian Cells," BioTechniques 20 (1996) pp. 116-121.
Chang et al., "Development of Peptide Antagonists for the Androgen Receptor Using Combinatorial Peptide Phage Display," Molecular Endocrinology 19(10), (2005) pp. 2478-2490.
Souriau et al., "New Binding Specificities Derived from Min-23, a Small Cystine-Stabilized Peptidic Scaffold," Biochemistry 44 (2005) pp. 7143-7155.
Lavallie et al., "A Thioredoxin Gene Fusion Expression System That Circumvents Inclusion Body Formation in the *E. coli* Cytoplasm," Bio/Technology 11 (1993) pp. 187-193.
Aronheim et al., "Analysis and Identification of Protein-Protein Interactions Using Protein Recruitment Systems," Methods in Enzymology 328 (2000) pp. 47-59.
Fearon et al., "Karyoplasmic interaction selection strategy: A general strategy to detect protein-protein interactions in mammalian cells," Proc. Natl. Acad. Sci. 89 (1992) pp. 7958-7962.
Osborne et al., "The Yeast Tribrid System—Genetic Detection of trans-phosphorylated ITAM-SH2-Interactions," Bio/Technology 13 (1995) pp. 1474-1478.
Nakai et al., "A Knowledge Base for Predicting Protein Localization Sites in Eukaryotic Cells," Genomics 14 (1992) pp. 897-911.
Barr et al., "Identification of the Critical Features of a Small Peptide Inhibitor of JNK Activity," The Journal of Biological Chemistry 277(13), (2002) pp. 10987-10997.
Barr et al., "The Critical Features and the Mechanism of Inhibition of a Kinase Interaction Motif-based Peptide Inhibitor of JNK," The Journal of Biological Chemistry 279(35), (2004) pp. 36327-36338.
Pero et al., "Identification of a Small Peptide that Inhibits the Phosphorylation of ErbB2 and Proliferation of ErbB2 Overexpressing Breast Cancer Cells," Int. J. Cancer 111 (2004) pp. 951-906.
Li et al., "Thermodynamic profiling of conformationally constrained cyclic ligands for the PDZ domain," Bioorganic & Medicinal Chemistry Letters 14 (2004) pp. 1385-1388.
O'Boyle et al., "Identification of a Novel Peptide Substrate of HSV-1 Protease Using Substrate Phage Display," Virology 236 (1997) pp. 338-347.

(Continued)

*Primary Examiner* — Michele K Joike
(74) *Attorney, Agent, or Firm* — Miles & Stockbridge PC

(57) ABSTRACT

A novel method of detecting and characterizing protein-peptide interactions is provided, which can be used for isolating peptides and proteins, respectively, as well as in drug screening and development.

12 Claims, 4 Drawing Sheets

(56) References Cited

OTHER PUBLICATIONS

Linn et al., "Using molecular repertoires to identify hi-affinity peptide ligands of the WW domain of human and mouse YAP," Biological Chemistry 378 (1997) pp. 531 (abstract only).

Larsson et al., "Quantitative codon optimisation of DNA libraries encoding sub-random peptides: design and characterisation of a novel library encoding transmembrane domain peptides," Nucleic Acids Research 30(23), (2002) pp. 1-8.

Park et al., "Progress in the development and application of computational methods for probabilistic protein design," Computers and Chemical Engineering 29 (2005) pp. 407-421.

Huang et al., "Molecular Biotechnology," 30 (2005) abstract.

Hu et al., "Large-scale mammalian cell culture," Curr. Opin. Biotechnol. 8 (1997) pp. 148.

Herzel et al., "Extracting information from cDNA arrays," CHAOS 11(1), (2001) pp. 98-107.

International Search Report, PCT/EP2007/007633, Jul. 3, 2008 (10 pages).

International Preliminary Report on Patentability, PCT/EP2007/007633, Aug. 31, 2007 (10 pages).

European Examination Report, EP 07 802 050.0, Jul. 24, 2009 (4 pages).

Arpmjeo, A et al.; Analysis and Identification of Protein-Protein Interactions Using Protein Recruitment Systems: Methods in Enzymology, Academic Press Inc, San Diego, CA, US, vol. 328, 2000, pp. 47-59, XP001147279, ISSN: 0076-6879.

Aronheim A et al.: "Isolation of an AP-1 Repressor by a Novel Method for Detecting Protein-Protein Interactions" Molecular and Cellular Biology, American Society for Microbiology, Washington, US, 3094-3102, XP000867026 ISSN: 0270-7306, 1997.

Aronheim Ami: "Ras Signaling Pathway for Analysis of Protein-Protein Interactions in Yeast and Mammalian Cells." Methods in Molecular Biology (Clifton, N.J.) 2004, vol. 250, 2004, pp. 251-262, XP009078616 ISSN: 1064-3745.

Lu Z et al: "Expression of Thioredoxin Random Peptide Libraries on the *Escherichia Coli* Cell Surface as Functional Fusions to Flagellin: A System Designed for Exploring Protein-Protein Interactions" Bio/Technology, Nature Publishing Co. New York, US, vol. 13, Apr. 1195 (Apr. 1995), pp. 366-372, XP002033346 ISSN: 0733-222X.

Colas P et al.: "Genetic Selection of Peptide Aptamers That Recognize and Inhibit Cyclin-Dependent Kinase 2" Nature, Nature Publishing Group, London, GB, vol. 380 Apr. 11, 1996, pp. 548-550, XP00090476 ISSN: 0028-0836 abstract.

Breuer et al., "Biochemical Indication for Myristoylation-Dependent Conformational Changes in HIV-1 NEF," Biochemistry, vol. 45, pp. 2339-1349—(2006).

Prinz et al., "The Role of the Thioredoxin and Glutaredoxin Pathways in Reducing Protein Disulfide Bonds in the *Escherichia coli* Cytoplasm," J Biol Chem. 1997;272(25):15661-15667.

Lipman et al., "Monoclonal Versus Polyclonal Antibodies: Distinguishing Characteristics, Applications, and Information Resources" ILAR J. 2005;46(3):259-268.

\* cited by examiner a) No protein-peptide interaction b) Protein-peptide interaction

MEANS AND METHODS FOR DETECTING PROTEIN-PEPTIDE INTERACTIONS

CROSS REFERENCE TO RELATED APPLICATIONS

This application is a §371 National Stage Application of PCT/EP2007/007633 Aug. 31, 2007 which claims priority to European Application 06018277.1 filed Aug. 31, 2006 and European Application 07016137.1 filed Aug. 16, 2007.

BACKGROUND OF INVENTION

1. Field of the Invention

The present invention generally relates to the technical field of molecular biology. More specifically, the invention relates to method for detecting and identifying peptides involved in protein-peptide interaction in cellular systems. In particular, the present invention relates to methods for detecting, identifying and optionally isolating peptides such as functional peptide ligands of target proteins.

2. Description of Related Art

Peptides show a wide variety of biological activities in cells one important example of which are natural peptide hormones acting as important molecular signals by binding to cellular receptors. It has also been shown that synthetic peptides can modulate the activity of proteins and even inhibit protein-protein interactions and are therefore important lead compounds in the field of drug discovery. Due to their high activity and specificity, during the last years there was an increased focus on peptides as therapeutic effectors.

The development of methods for detecting interactions between target proteins and peptides under physiological conditions is of major interest. Although there exists already a number of methods for detecting interactions between proteins and peptide ligands as well as for isolating novel peptide ligands, in particular, methods for identifying novel peptide ligands are of special interest in drug discovery. However, existing in vitro methods for the identification of binding peptides (Liu et al., Exp. Hematology 31 (2003), 11-30) require as a prerequisite the purification of the protein of interest, resulting in most cases in a decreased biological activity and binding quality, since many target proteins adopt their preferred conformation exclusively in the cytoplasm which can differ from their conformation under non-physiological conditions.

One common method for isolating peptide ligands allowing the presentation of peptide libraries on the surface of a filamentous phage (Smith, Science 228 (1985), 1315-1317), comprises the introduction of exogenous peptide sequences into the genome of phage capsid proteins, because of which this method is also referred to as phage display technology. International application WO95/31723 describes the use of this method for in vitro selection of peptides from biological peptide libraries, but although there are few examples for its application to living organisms (Arap et al., Proc. Natl. Am. Soc. 99 (2002), 1527-1531), its use for in vivo selection is limited.

To date, there exist different methods for identifying binding partners in cellular systems. In this context, yeast as a eukaryotic cell is a preferred organism to analyze protein-protein interaction in vivo. One characteristic method using yeast as a preferred organism is the yeast two-hybrid system, which represents a further development of the two-hybrid protein interaction assay (Fields and Song, Nature 349 (1989), 245-246). These cellular methods comprise one binding partner fused to a DNA binding domain, while the respective other binding partner is fused to a strong transcription activation domain, and as a result of the molecular interaction of the partners the generation of a functional transcription factor, leading to a change in phenotype of the cell due to expression of respective genes.

However, since the above-mentioned methods are based on the detection of transcriptional activation, they have several drawbacks such as the generation of false positive responses, since many proteins containing transactivation as well as DNA binding domains can activate the system without a respective interaction. Furthermore, since transcription occurs in the nucleus, the above-mentioned methods are neither appropriate for investigating proteins which are toxic to cells when expressed in the nucleus nor proteins mainly acting in the cytoplasm, because of which those proteins obviously cannot be analyzed.

Hence, there is still a need for assays detecting interactions between proteins and peptides under physiological conditions in living cells.

SUMMARY OF THE INVENTION

The present invention overcomes the drawbacks of the prior art by providing the embodiments characterized in the claims and described further below. In particular, the present invention provides a method which is easy to perform and does not only allow for investigation of cytosolic proteins, transcription factors and small peptides but also provides a method which by its easy way to handle is suitable for being used in high throughput screening. The simplicity/convenience of the method of the present invention due to for example the use of cell growth as altered phenotype upon protein-peptide interaction, i.e. as signal indicating whether or not the intended interaction of interest has occurred allows an easy detection of effect/result and renders it advantageous over the prior art.

In general, the present invention concerns methods for detecting interactions among proteins and peptides. Accordingly, in one aspect, the present invention relates to a method of determining whether a first protein is capable of physically interacting with a second protein, i.e. peptide within a cell featuring the use of a fusion of a target protein and an effector molecule, and a peptide which is conformationally stabilized by linkage to a carrier protein and directed through fusion with an additional domain to a particular cell compartment. The method and assay of the present invention combines the reliability of biochemical in vitro or simple two hybrid assays for protein-protein/peptide interactions and the validity of complex in vivo investigations aiming at elucidating the interaction of a given protein with its binding ligand.

Since usually the target protein will be predetermined while the interacting peptide(s) remain to be identified the target protein may also be considered as "bait" and the interacting peptide(s) as "prey". However, the person skilled in the art will immediately recognize that the method of the present invention can also be performed vice versa. Those skilled in the art will also recognize that the bait and prey protein/peptides may be derived from any appropriate eukaryotic or prokaryotic source, including yeast, mammalian cell, and prokaryotic cell genomes or cDNAs as well as artificial sequences. The present invention further provides a drug screening assay useful for identifying a drug that can alter a particular protein-protein/peptide interaction or modulate the activity of a target protein. In addition, the present invention provides a kit useful for performing the screening assay.

(a) illustrates the growth of yeast Cdc25-2 yeast cells at a restrictive temperature (37° C.) as a function of the interaction of the protein c-jun N-terminal kinase (JNK) and the peptide JIP20, in the course of which the Ras protein fused to the protein (JNK) is recruited to the membrane and as a consequence activating the Ras signalling pathway, allowing the yeast cells to grow even at the restrictive temperature. Cell growth is shown in dependency of the simultaneous expression of both fusion proteins, the expression of which is induced by galactose, since it is regulated by a GAL1-promoter. As expected, cell growth at the restrictive temperature is only detected upon galactose addition (left part) whereas addition of glucose did not show any cell growth (right part). Thus, growth only occurs after Ras is recruited to the membrane.

Hence, after induction of gene expression by addition of galactose, both fusion proteins (protein 1, comprising Ras and protein 2, comprising the localization domain) are expressed, allowing for an interaction of JNK with JIP20 and as a result the recruitment of Ras to the membrane where it exerts its effect in activating the Ras signalling pathway as a result of which the phenotype of cells is altered in that they can grow even at restrictive temperature of 37° C. The abbreviations wt, APF, K55A represent different JNK variants and pADRS represents a control, i.e. empty vector; for details see Example 1.

(b) illustrates a control experiment where cells were with JNK1 constructs identical to (a), but with a different thioredoxin-JIP20 construct (empty vector), i.e. a construct, entirely lacking JIP20. As demonstrated, cell growth is dependent on the expression of JIP20 but not on the expression of thioredoxin alone, since no cell growth is detectable, again proving that the expression of JIP20 and its interaction with JNK, respectively, as well as the subsequent recruitment of Ras to the membrane accompanying this interaction is important. Since no interaction of JNK1 with JIP20 was possible due to lack of JIP20, no cell growth is detectable. A general failure of this approach was excluded by applying a "positive control", i.e. proteins, the expression of which is also induced by galactose and the interaction of which is known to lead to the respective cell growth, those proteins in the present case being cyclin dependent kinase (CDK4) and cyclin dependent kinase inhibitor (p16). Again, as expected, addition of glucose did not induce the thioredoxin expression and did not lead to the growth signal.

Figure 3:
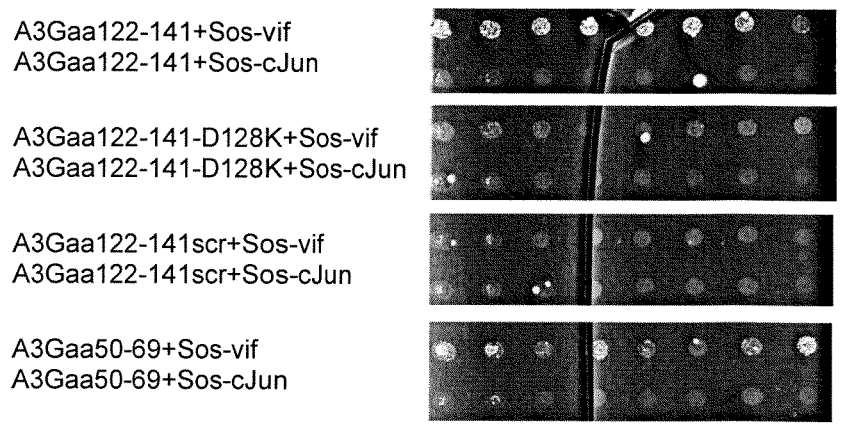

FIG. 3: shows interaction analysis of Apobec3G derived peptides with Vif on galactose plates at the restrictive temperature of 37° C. Growth of yeast cells is dependent on the interaction between peptide and Vif protein and can be observed with peptide A3Gaa122-141 (SEQ ID NO: 10) and peptide A3Gaa50-69 (SEQ ID NO: 8). By transformation with a control plasmid instead of Vif no growth was observed for all peptides.

Figure 4:
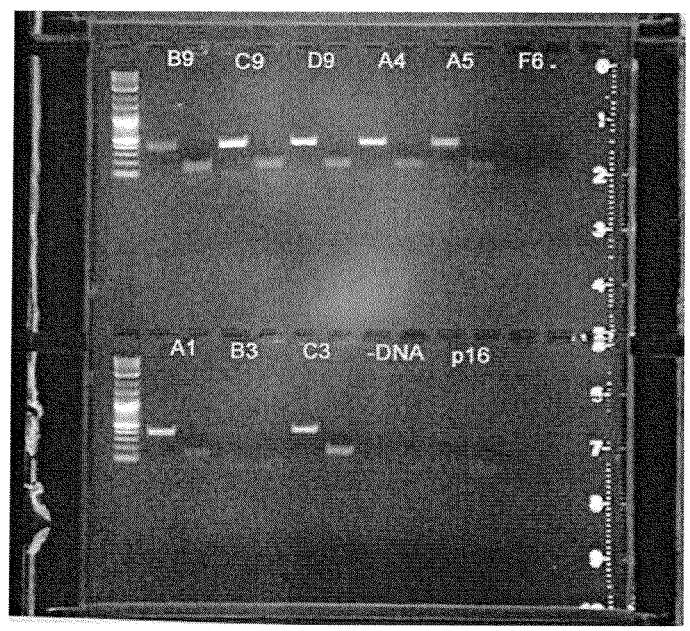

FIG. 4: shows a photo of an agarose gel. DNA fragments, i.e. PCR products amplified with primers specific for thioredoxin and JIP15, respectively, are shown representing yeast clones being positive for the existence of a thioredoxin fragment as well as for the existence of a JIP15 fragment; for detail see also Example 3. As demonstrated, clones B9, C9, D9, A4, A5, A1 and C3 were positive for the existence of a thioredoxin fragment as well as for the existence of a JIP15 fragment. However, although a positive PCR result was not obtained for clones B3 and F6, they were also defined as positive according to the results in growth analysis. Those clones could express interacting proteins from the Hela library.

Figure 5:
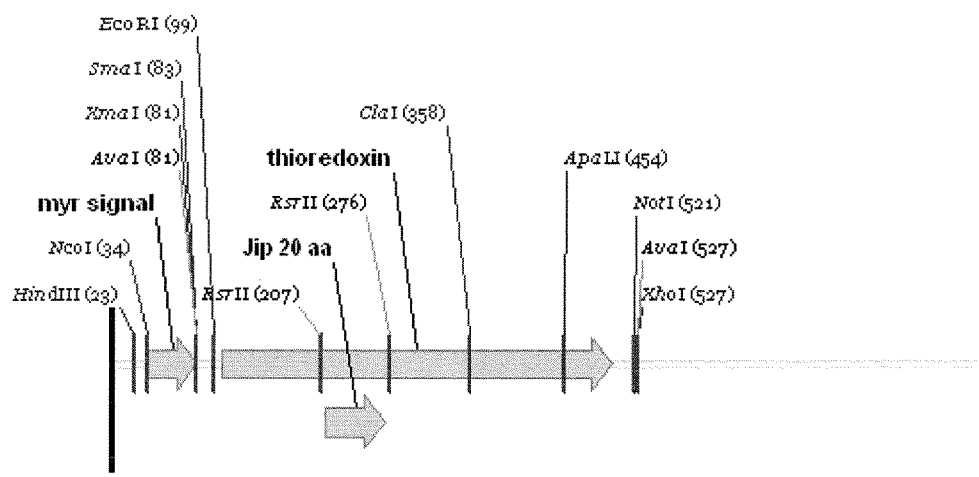

FIG. 5: schematically represents a linearized plasmid based on pYES (Invitrogen). The sites of inserted myristoylation signal, JIP20 and thioredoxin, respectively, as well as restriction sites are indicated.

DEFINITIONS

"conformationally stabilized" as the term is used herein, generally refers to a peptide or protein, having reduced flexibility due to its amino and carboxyl terminus, respectively, fixed in space, wherein the conformationally stabilized peptide or protein is preferably presented in a structurally rigid manner. Conformational stabilization can be facilitated by embedding the protein or peptide of interest within a conformation-stabilizing molecule such as a conformation-stabilizing protein, for example a carrier-protein.

"candidate peptide" and "candidate protein", respectively, as the term is used herein, generally describes a peptide and a protein, respectively, being a candidate for an interaction with a partner of interest.

"agonist" and "antagonist", as the term is used herein, generally describes an interacting molecule having the ability to increase (agonist) or decrease (antagonist) production of the respective signal.

"randomly generated", as the expression is used herein, generally relates to sequences being not predetermined.

"intentionally designed", as the term is used herein, generally refers to sequences having a certain DNA or protein sequence or motif determined prior to their synthesis.

DETAILED DESCRIPTION OF THE INVENTION

The present invention provides a method for detecting protein-peptide interactions in vivo and isolating the respective interaction partner(s). More specifically, the method of the present invention is based on detecting molecular interaction of a target protein "bait" which is linked to an effector molecule thereby generating a hybrid molecule, and a peptide "prey" or a population of potential interacting peptides which are conformationally stabilized by linkage to a carrier protein which contains a cell compartment localization domain. In particular, this interaction is detected by a signal that is induced by the respective effector molecule which by binding of "bait" and "prey" is recruited to a specific cell compartment, wherein the recruitment is due to locally restricted presentation of the "prey" at the respective cell compartment where the effector then exerts its effect.

Figure 1:
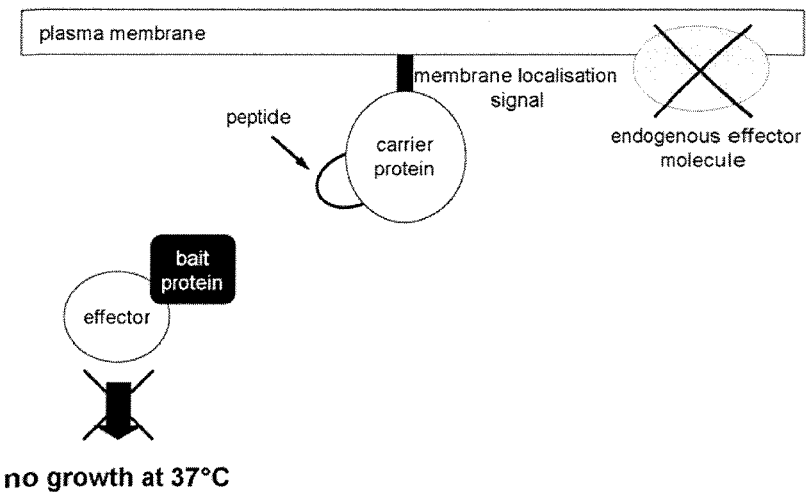
FIG. 1: illustrates schematically the analysis of a protein-peptide interaction in cells according to the method of present invention.
Figure 1:
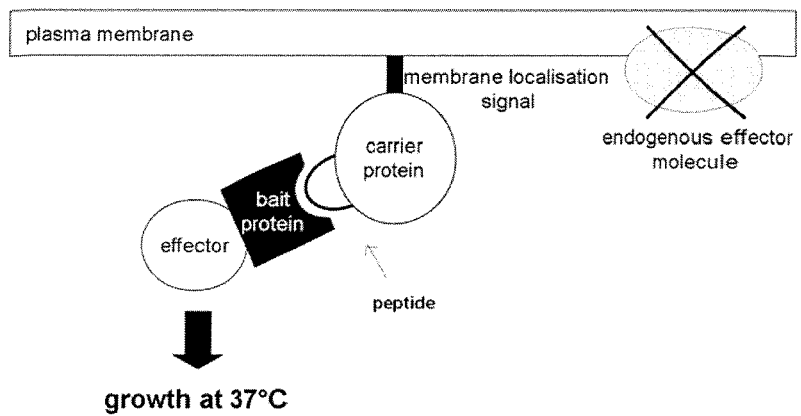
Figure 2:
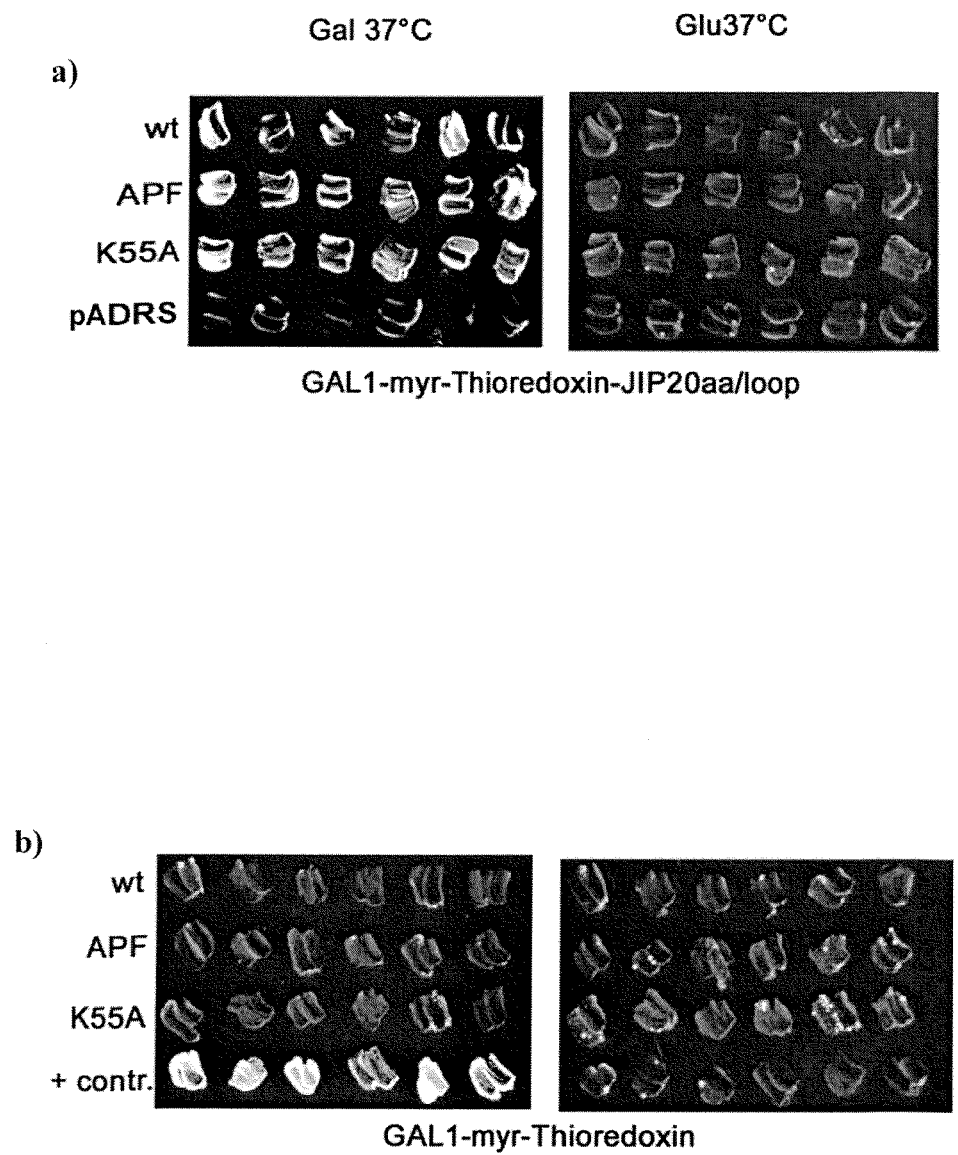
FIG. 2: generally illustrates growth of yeast cells in dependency of the simultaneous expression of two fusion proteins (fusion protein 1, the "bait", comprising the Ras-protein and JNK and fusion protein 2, the "prey" comprising a membrane localization domain, the carrier protein thioredoxin and the peptide JIP20, intended to intract with the JNK upon binding of "bait" and "prey". In particular, FIG. 2 shows the interaction of the "bait" which is expressed in context of fusion protein 1 comprising the protein of interest and a respective effector and the "prey", i.e. the peptide of fusion protein 2, which is localized to cell-membrane. Ras protein as the exemplified effector used in the Examples of the present invention is recruited to the compartment (here: plasma membrane) where the "prey" which is intended to interact with the "bait" is localized due to its membrane localization domain. Upon recruitment of Ras (bound to "bait") to the membrane, Ras-pathway is activated which results in a detectable phenotype such as cell growth of yeast cells at a restrictive temperature of 37° C.

As demonstrated in the examples, the present invention provides an "easy to perform"-method, capable of specifically detecting protein-peptide interactions by inducing an effector-mediated signal, such as cell growth; see also FIG. 2. Furthermore, FIG. 2 illustrates the specificity of the protein-peptide interaction as well as the simplicity of its detection by monitoring cell growth. As cell growth is detectable upon addition of galactose the signal is specific and easy to detect and interpreted. It is a simple "yes or no"—answer not requiring any gradual analyses. Hence, the present invention significantly contributes to the investigation of protein and peptide-ligand interaction which hitherto was difficult if at all to be accomplished.

Thus, in one aspect the present invention relates to a method of identifying a protein-peptide interaction or isolating a partner of a protein-peptide interaction, comprising:
(a) providing within a host cell
  (i) a hybrid molecule, comprising a target protein and an effector;
  (ii) a peptide or a population of peptides, wherein the peptide is linked to a carrier protein, said carrier protein being linked to a cell compartment localization domain; and
(b) detection of a signal identifying the protein-peptide interaction of the hybrid molecule and the peptide; and optionally
(c) isolating a partner of the protein-peptide interaction based on its ability to alter the signal when present, preferably wherein the hybrid molecule is a fusion protein.

Effectors and effector molecules, respectively, are well known to mediate effects, which in their absence do not or only less occur. Mediating comprise a plurality of processes such as providing efficiency and specificity in cell signalling itself as well as in the coordination of signalling processes and in this context, especially compartmentalized signalling, i.e. the transfer of a signal from one cell compartment to another. Although there is a broad range of effector molecules having localized activity, such as scaffold, anchor and adaptor proteins, effector molecules which are especially involved in compartmentalized signalling comprise for instance G-proteins, protein kinases, protein phosphatases and Ras-proteins, just to name a few, which mediate for example activation of the phosphatidylinositol 3-kinase pathway, the compartmentalized cAMP signalling and the Ras/MAPK signal transduction pathway.

As known to the person skilled in the art, detecting such a mediated effect requires the absence of the same, i.e. of said effect, if the effector is not present. Thus, in a further preferred embodiment, the host cell used in the method of the present invention is lacking an active endogenous effector.

A further advantage of the method of the present invention is that numerous effector molecules are applicable. One component of the method and assay of the present invention, i.e. the recruitment of an effector protein, which is not a transcription factor, to a particular cell compartment, where the effector protein can activate a reporter molecule is disclosed in U.S. Pat. No. 5,776,689. The protein recruitment system is exemplified therein using a yeast cell based assay, in which a protein-protein interaction results in the recruitment of a guanine nucleotide exchange factor (GEF) to the plasma membrane, where the GEF activates a Ras reporter molecule, resulting in the survival of cells that otherwise would not survive under the particular cell culture conditions. However, although the method and assay of the present invention does not consist of the protein recruitment system described in U.S. Pat. No. 5,776,689 per se, it employs elements of the respective system. Therefore, the disclosure content of the above-referenced US patent as well as that of the publications cited therein is incorporated herein by reference for the purpose of providing information on one or more elements of the present invention, in particular target proteins such as Ras and effector molecules such as guanine nucleotide exchange factor that is known to the person skilled in the art including nucleotide and amino acid sequences of the appropriate proteins. In this context, unless stated otherwise the term "effector molecule" and "effector protein", respectively, is used as defined and explained in this US patent. The same applies to the "active endogenous effector protein" and the lack of it, respectively. In addition, as used herein, the term "cell compartment" and "cell compartment localization domain" equate to the corresponding terms in U.S. Pat. No. 5,776,689 which also contains ample examples of useful domains that can be applied in accordance with the present invention as well; see for example the amino acid sequences of SEQ ID NOs. 1 to 3 therein. Accordingly, also for the purpose of providing information on cell compartment localization domains the disclosure content of U.S. Pat. No. 5,776,689 and the publications cited therein is incorporated herein by reference. Likewise, appropriate cells and cell lines, e.g. *S. cerevisiae* cdc25-2 cells and NIH 3T3 cells are described. In addition, this US patent contains useful information on the identification and elimination of "false positives", which for this purpose is also incorporated herein by reference.

The "Sos Recruitment System" (SRS) and particularly the "Ras Recruiting System" (RRS), the latter making use of cells which are not able to express functional Ras due to the fact that the GTP/GDP exchange factor of Ras is mutated such that it cannot be localized at the membrane, e.g. lacking the farnesylation box or having a mutation therein, are described in international application WO00/05410 and references cited therein, the disclosure content of which is incorporated herein by reference for the purpose of providing information on RRS and components thereof that is known to the person skilled in the art including nucleotide and amino acid sequences of the appropriate proteins, cloning and expression vectors, cells such as yeast cdc25 mutant strains, culture conditions, etc, for performing the protein-protein interaction assay described therein, and which can be used and adapted in accordance with the present invention as well.

Although the Sos-recruitment system generally described in U.S. Pat. No. 5,776,689 describes protein-protein interactions, it is silent to interactions between proteins and peptides. In this context, the method of the present invention is different in that it allows the identification of interactions between proteins and peptides, in particular small peptides, comprising for example only 20 amino acids as described in example 1 or 2. Without intending to be bound by theory, this is believed to be particularly enabled by the way how according to the method of the present invention the candidate peptides are presented, which is presented in context with the modified SRS used herein; see also the examples which illustrate preferred embodiments of the present invention.

Thus, besides its easy way to perform, the method of the present invention is particularly suited for investigating the interaction of proteins and peptides, in particular small peptides, which renders the method superior to the above-referenced prior art methods.

Similarly, the present invention is superior to the Ras-recruitment system (RRS), described in for example international application WO00/05410, since with respect to the detection of interactions between proteins and peptides, the RRS is afflicted with the same drawbacks as already discussed above in context with U.S. Pat. No. 5,776,689.

Nevertheless, since as already mentioned, the method of the present invention makes use of elements of the protein recruitment system described in U.S. Pat. No. 5,776,689, the content of which is incorporated herein by reference, in accordance with the method of the present invention, guanine nucleotide exchange factor (GEF), preferably the Sos-protein, most preferably the human Sos-protein (h-Sos) can be used as effector molecule. In another preferred embodiment, the effector used in accordance with the method of the present invention comprises the Ras-protein, preferably the human Ras-protein (h-Ras). Most preferably, a mutated Ras-protein which cannot localize to the cell membrane and does not require an exchange factor is used as the effector molecule, e.g., a Ras-protein lacking a farnesylation box, the latter of which is also exemplified in the examples conducted in accordance with the present invention. Since the Ras-protein is a GTP-bound Ras-protein (Q61 L) without membrane localization domain (ΔF), only in case of a molecular interaction of the target protein with the peptide and as consequence recruitment of Ras to the membrane, a detectable Ras-mediated signal transduction at the plasma membrane is detectable. Therefore, in the preferred embodiments the detectable signal will be due to the activation of the Ras-protein.

As it is well known in the art and as already mentioned above, for the detection of an effect, which is mediated by an effector, the absence of said effect is mandatory in the absence of the effector. Hence, for detecting activation of, for example, the Ras signalling pathway, it is obvious that the pathway should not be activated without the effector. Therefore, organisms, cells, cell lines or cultures, known to those skilled in the art have to be prepared in that they lack the possibility to self-activate the Ras signalling pathway and therefore to be dependent on an effector such as Ras-protein, which according to the present invention is only recruited to its site of action, i.e. the membrane, upon the aforementioned interaction of a target protein being fused to a Ras protein lacking the ability to localize itself to the membrane, and a peptide which is linked to a protein having a membrane localization domain and thereby being localized at the membrane.

One major advantage of the method of the present invention is that the activation of the Ras signalling pathway upon the aforementioned interaction can be easily detected by, for example, an altered phenotype of a host cell, such as growth of cells, which are under restrictive conditions defective in producing a detectable Ras-signal without the above described interaction. In this context, one major advantage of the method according to the present invention is that the use of Ras-proteins as effector molecules, having no DNA binding or transcriptional activity, allows for the investigation of transcription factors as target proteins, since in comparison to DNA binding domains as effectors and transcriptional activation as readout, those hybrid molecules are not auto active without interaction.

A further major advantage of the method of the present invention is that it can be applied to almost any type of cell, such as mammalian, avian, insect, yeast and *E. coli* cells. However, in one preferred embodiment, the host cell used in the method according to the present invention comprises an eukaryotic cell, preferably a yeast cell; see also supra. Thus, while yeast cells are preferred a plurality of other eukaryotic cells can be used, in particular mammalian cells such as CHO, HEK, COST, 3T3, or 293 cells.

As it is known, within a cell Ras-proteins are present in their inactive form, i.e. bound to GDP (Ras-GDP) showing no signalling activity. By contrast, in its active form, i.e. bound to GTP (Ras-GTP) those proteins mediate signalling processes from the plasma membrane to the nucleus, wherein the activation of Ras is controlled by guanosine exchange factors (GEFs), which convert inactive Ras-GDP to active Ras-GTP. As discussed above, if activation of the Ras signalling pathway is the signal to be detected it is suitable to use cells being devoid of functional Ras and therefore having a phenotype which is altered depending on the presence and absence of Ras. Thus, the cells used in the method of the present invention are defective in providing a functional Ras.

As mentioned above, to investigate the effect of protein-peptide interaction, i.e. the recruitment of Ras to the membrane, it is necessary to use cells the phenotype of which changes upon Ras-recruitment to the membrane. Therefore, in the examples of the present invention yeast cells were used being mutated in cdc25 (cdc25-2), Cdc25 being a GEF that when localized at the plasma membrane, leads to the activation of Ras; see Petitjean et al., Genetics 124 (1990), 797-806. The temperature sensitive Cdc25-2 mutation, however, cannot express a functional Ras effector, i.e. cannot activate Ras at the restrictive temperature of 37° leading to cells having a phenotype of a growth defect at the respective temperature, a phenotype which is also found in other organisms like *S. pombe, Drosophila* and different mammalian cells. The person skilled in the art will easily know how to "generate" a defective effector, for example, either by mutating the effector itself of by mutating proteins that influence its activity or also changes in the expression level as well as external conditions can influence effector activities. However, this defect can be overcome by Ras-activation upon the protein-peptide interaction, described in the examples of the present invention.

Thus, in a particularly preferred embodiment of the method of the present invention, the yeast cells are *Saccharomyces cerevisiae* cdc25-2 cells. Especially in this embodiment, the detectable signal is preferably cell growth at the non-permissive temperature of the host cell, for example, at 33-37° C. However, besides the phenotype of cell growth, the skilled artisan will easily understand that there are several phenotypes and effects, respectively, which depending on the experimental setup can be altered, i.e. represent a measurable change in response to an interaction between a "bait" molecule and a "prey" molecule, such as accumulation of substances, activation of genes as well as any changes in fluorescence activity.

As mentioned, the present invention provides a method for detecting peptide-protein interaction as well as identifying and isolating novel candidate peptides for interaction with a respective target protein. Although the method of the present invention is useful for investigating a wide variety of different therapeutic target proteins, in a preferred embodiment the target protein used in the method of the present invention is selected from the group consisting of kinases, viral proteins, nuclear receptors, transcription factors, membrane proteins, phosphatases, ubiquitinating enzymes, and preferably comprises a kinase or a viral protein. More preferably, the viral protein is HIV Vif protein and the kinase is a c-Jun N-terminal kinase (JNK), most preferably a mutated JNK, such as JNK APS, JNK K55A, or JNK wt.

During experiments performed in accordance with the present invention, however, it turned out that the method of the present invention maybe further improved by using a linker arranged between the effector molecule and the protein leading in some cases to a further improved interaction of protein and peptide. In particular, a peptide linker, preferably having the sequence Gly-Gly-Gly-Gly-Ser-Gly-Gly-Gly-Gly-Ser (SEQ ID NO: 1) and the description of which or similar can be found in, for example, Evers et al., Biochemistry 45 (2006), 13183 and Maeda et al., BioTechniques 20 (1996), 116 may be used. Therefore, in some embodiments, the method of the present invention further comprises providing within a host cell a hybrid molecule, comprising a target protein and an effector linked by peptide linker, for example, when investigating interaction of peptides and a viral target protein such as the HIV Vif protein.

As mentioned above, the target protein exemplified in the examples of the present invention, is the c-Jun N-terminal kinase (JNK) which is a member of the family of serine and threonine mitogen-activated protein kinases and is involved in signal transduction of numerous physiological processes, including tissue differentiation and pathogenesis. To date, three genes encoding for JNKs have been identified and ten isoforms resulting from alternative splicing of these genes have been described. JNKs have been implicated in several important diseases including cancer, diabetes, and neurodegenerative diseases.

In the context of the experiments conducted in accordance with the present invention, the interaction of JNKwt (JNK1α2), as well as that of different mutants of JNK with the peptide JIP20 having the sequence GPGDTYRPKRPTTLN-LFPQVPRSG (SEQ ID NO: 6) could be detected by the method of the present invention; see example 1. Furthermore, the interaction of a viral protein, HIV Vif, with the peptides A3Gaa50-69 having the sequence DAKIFRGQVYSELKY-HPEMR (SEQ ID NO: 8) and peptide A3Gaa122-141 having the sequence RLYYFWDPDYQEALRSLCQK (SEQ ID NO: 10) was detected when using the method of the present invention (see Example 2) which hitherto have not been described in the field of HIV, in particular not as binding to Vif.

The person skilled in the art will easily recognize, that the application of the present method is not restricted to these examples and that also other protein-peptide interactions are well detectable and may prove the applicability of the method of the present invention, for example, the interaction of the human androgen receptor as target protein with the peptide 622, the interaction of which is known and described in for example Chang et al., Mol. Endocrinol. 19 (2005), 2478-2490. The human androgen receptor is a member of the family of nuclear hormone receptors, i.e. a family of ligand dependent transcription factors which are key regulatory proteins in diverse physiological processes including embryogenesis, sexual development, energy homeostasis, and fat metabolism.

Statistical evaluations of amino acids involved in protein-peptide interactions strongly suggest that proteins recognize and interact with peptides preferably through a restricted set of specialized interface amino acid residues, such as Pro, Ile, Tyr, Trp, Asp and Arg (Sillerud and Larson, Current protein and peptide science 6 (2005), 151-169), since these amino acids represent residues from each of the three classes of amino acids, i.e. hydrophobic, aromatic and charged, having one anionic and one cationic residue at neutral pH. In this context, the use of a carrier protein turned out be a further major advantage of the method of the present invention ensuring a functionally stabilized presentation of the peptide and preventing disturbing interactions of the peptide with the respective cellular compartment, e.g. the plasma membrane, such as the interaction of polar amino acids with hydrophilic head groups of the phospholipid membrane or insertion into it. Additionally, the carrier protein is able to provide protection from proteolytic degradation.

For the purposes of the present invention, especially small proteins of known structure are useful as carrier proteins. As exemplified in the examples of the present invention, in a preferred embodiment, the carrier protein used in accordance with the method of the present invention is thioredoxin or a thioredoxin-like molecule, although other molecules such as green fluorescent protein, Z-domain of protein A, tendamistat, Kunitz domain, fibronectin type III domain, lipocalin, basic pancreatic trypsin inhibitor and conotoxine can also serve as carrier; see Souriau et at, Biochem 44 (2005), 7143-7155.

As demonstrated in the examples, thioredoxin and thioredoxin-like conformation-constraining proteins are the most preferred carrier proteins to be used in the method of the present invention. Unless indicated otherwise, the term "conformation-constraining protein" is used in accordance with the definition provided in international application WO96/02561 meaning any peptide or polypeptide which is capable of reducing the flexibility of another protein's amino and/or carboxy termini. Preferably, such proteins provide a rigid scaffold or platform for the protein of interest. Examples of conformation-constraining proteins include thioredoxin and other thioredoxin-like proteins as disclosed, for example, in mentioned international application WO96/02561. Accordingly, although the method and assay of the present invention does not consist of the protein-protein interaction system described in international application WO96/02561 per se, but rather makes use of some elements thereof, the disclosure content of this application as well as that of the publications cited therein is incorporated herein by reference for the purpose of providing information on thioredoxin-like proteins including nucleotide and amino acid sequences of the appropriate proteins. Furthermore, the utility of thioredoxin or other thioredoxin-like proteins is described in U.S. Pat. No. 5,270,181 and by LaVallie et al., Bio/Technology 11 (1993), 187-193, the content of which is hereby incorporated by reference.

*Escherichia Coli* thioredoxin has previously been used in the expression of a combinatorial library of constrained 20-residue peptides displayed by the active-site loop of thioredoxin in a yeast two-hybrid system to select those peptides that bind human Cdk2; see Colas et al., Nature 380 (1996), 548-550. However, the peptides so identified did not show any notable sequence similarity to known proteins but formed new recognition structures and did not compete in binding with cyclin E, the natural protein interaction partner of CdK2. Hence, the thioredoxin display system was able to identify artificial peptide aptamers that mimic the recognition function of antibodies, but that are structurally unrelated to the target protein and its natural protein binding partner, respectively.

This finding seemed to render the thioredoxin display system unsuitable for the purpose of identifying protein-protein interactions which actually take place in the cell, for example, in order to unravel and analyze complex signal transduction pathways. Furthermore, knowledge of protein-protein interaction in vivo is necessary in order to provide means to screen for drugs that specifically interfere with said interaction; see for example U.S. Pat. No. 5,776,689.

In accordance with the present invention it could surprisingly be shown that the use of a carrier protein, in particular thioredoxin to present a given peptide to the putative protein binding partner of its cognate full-length protein in a cellular assay provides a substantial improvement of identifying protein-peptide interactions, since peptides can be identified which correspond to the putative protein binding domain of the target interaction partner in vivo; see, e.g., Example 2.

In preferred embodiments of the present invention for detecting protein-peptide interactions, the intracellular peptide is embedded within the conformation-constraining carrier-protein, preferably thioredoxin, wherein the peptides can either be directly linked to the C-terminus or N-terminus of the carrier-protein, or alternatively be inserted in the carrier protein through disulfide bonding of suitably located cysteine residues and for example be presented as inserts in the active-loop of thioredoxin.

For the sake of information it is noted that in one embodiment, the method and assay of the present invention does not comprise or consist of the split-ubiquitin system as specifically disclosed and claimed in international applications WO02/27020 and WO03/083136. However, the description of these applications may contain useful information on molecular biological tools and materials such as vectors, cells, nucleic acid library construction, compound libraries and collections, etc., which may employed in accordance with the teaching of the present invention. Accordingly, the disclosure content of international applications WO02/27020 and WO03/083136 as well as that of the publications cited therein is incorporated herein by reference for the purpose of providing information on the appropriate proteins, cloning and expression vectors, cells, culture conditions, etc, for performing and analyzing the result of protein-protein interaction assays. Furthermore, the disclosure content of international application WO03/083136 is particularly incorporated herein by reference for the purpose of information on the identification/design of scFVs or antibodies that are capable of interfering with protein-protein interactions and the identification of compounds that bind to and activate G protein-coupled receptors (GPCRs) or that selectively bind to and activate one GPCR but not another GPCR that is co-expressed within the same cell.

Furthermore, since the present invention does not necessitate the use of a transcription factor as the effector protein, preferred embodiments of the present invention are distinguishable from the two hybrid assay; see Fields and Song, Nature 340 (1989), 245-246; U.S. Pat. No. 5,283,173, each of which is incorporated herein by reference and variations thereof; see, for example, Fearon et al., Proc. Natl. Acad. Sci., USA 89 (1992), 7958-7962, and Osborne et al., Biotechnology 13 (1995), 1474-1478, each of which is incorporated herein by reference. Furthermore, the protein-peptide interaction assay of the present invention involves the translocation of an effector protein to the cell compartment containing a reporter molecule, thus further distinguishing the invention from the two hybrid assay.

As mentioned hereinbefore, another component of the method of the present invention is directing the putative interacting peptide(s) to a particular cell compartment, for example, through the use of a corresponding cell compartment localization domain linked to the peptide via the carrier protein, preferably within a fusion protein. Cell compartment localization domains in general mediate localization of the respective molecule such as peptide or protein to a predetermined compartment. This can be any compartment within a cell, to which a respective protein can be localized. There are various compartments known to the person skilled in the art such as the plasma membrane, the nucleus, the mitochondrial membrane, the endoplasmatic reticulum (ER), the Golgi apparatus as well as cell compartments of plant cells like the vacuole and the chloroplast. To render an intended molecule localized at the respective compartment, the molecule of interest is usually provided with a respective domain, enabling the aforementioned localization, i.e. to, for example, attach to or integrate in a certain compartment or parts thereof.

Various cell compartment localization domains are known to the skilled person such as membrane localization signals, nuclear localization signals, and ER- or a mitochondrial localization sequences, just to name a few; see for example Nakai and Kanehisa, Genomics 14 (1992), 897-911. The cell compartment localization domain which according to the method of the present invention is linked to the carrier protein, either N- or C-terminally, determines the accessibility of the peptide or population of peptides presented. As exemplified within the examples of the present invention, the cell compartment localization domain comprises a polypeptide sequence that directs translocation of the carrier-peptide hybrid molecule to a particular cell compartment. In a preferred embodiment, the cell compartment localization domain used in accordance with the method of the present invention is a membrane localization domain, preferably a plasma membrane localization domain and most preferably a myristoylation signal.

As already mentioned above, the investigation of protein-peptide interactions comprising a short peptide as candidate, i.e. as a potential interacting partner, is difficult due to sterical hindrance of the interaction or even insertion of the peptide into the membrane. Therefore, the present invention is especially suited to also investigate those interactions, since the binding of a short peptide or its embedding in a carrier protein not only prevents from the afore-mentioned drawback by providing a "spacer", but also conformationally stabilizes the peptide.

Although peptides with similar amino acid sequences have already been shown to interact with JNK using alternative experimental methods (Barr et al., J. Biol. Chem. 277(13) (2002), 10987-10997, Barr et al., J. Biol. Chem. 279 (41) (2004), 42178-42189), the detection of interaction of JNKwt as well as selected JNK-mutants and the peptide JIP20 GPGDTYRPKRPTTLNLFPQVPRSG (SEQ ID NO: 6) demonstrates that the method of the present invention allows for detection of specific binding to even small peptides, especially regarding the fact that JIP20 comprises 20 amino acids of the sequence of the JNK interacting protein 1 (plus 4 amino acids of linker), containing a number of charged (Arg, Lys, Asn, Gln) and hydrophobic (Leu, Val, Phe) amino acid residues which in another method being devoid of the advantages of the present invention i.e. having no carrier molecule to which the peptide is linked could result in unspecific interactions with the plasma membrane and other cell compartments.

Furthermore, identification of the interaction of Vif with the peptides A3Gaa50-80 (SEQ ID NO: 8) and A3Gaa122-141 (SEQ ID NO: 10), which are derived from the human apolipoprotein B mRNA-editing enzyme catalytic polypeptide-like-3G (APOBEC3G), a cellular protein involved in the cellular defence against HIV-infection, proves the specificity and sensitivity of the method, since the respective interaction was not revealed using the conventional methods described in the art.

As demonstrated in examples 1 and 2, unintended and unspecific binding is prevented by the use of a carrier molecule in the method of the present invention. Therefore, in a particular preferred embodiment the peptide used in accordance with the method of the present invention is imbedded within the carrier protein.

The person skilled in the art will easily understand that a broad variety of peptides are suitable to be used in the present invention. In one embodiment the peptide used in accordance with the method of the present invention comprises a randomly generated or (intentionally) designed sequence. For example, the amino acid sequence of the peptide to be used does not match exactly a corresponding stretch of amino acid sequence of any given native protein, in particular human and viral protein, respectively. In another embodiment, a peptide is used comprising 10 to 30 amino acids in length, preferably 15 to 25 amino acids, and more preferably 20 to 25 amino acids. In one particular embodiment the peptide essentially consists of the amino acid sequence GPGDTYRPKRPTTLNLFPQVPRSG (SEQ ID NO: 6), DAKIFRGQVYSELKYHPEMR (SEQ ID NO: 8), or RLYYFWDPDYQEALRSLCQK (SEQ ID NO: 10). However, peptides comprising one or two further amino acids either at the C- or N-terminus as well as fusions thereof with heterologous molecules may show similar properties and therefore are encompassed in the present invention as well. Furthermore, the skilled artisan will recognize that also library encoded peptides can be used in the method of the present invention.

Random or designed peptide-encoding libraries may be used in accordance with the present invention for selecting and screening, respectively, as well as for identifying candidates of novel protein-interacting peptides. Respective libraries are known to the skilled artisan; see also the prior art cited supra. As exemplified in example 3, the method of the present invention can be used for identifying interacting peptides within a population of DNA encoded proteins or peptides, wherein the population can comprise randomly generated as well as designed peptides. Thus, in a further preferred embodiment, the present invention relates to a method of detecting and/or isolating an interacting peptide in a population of peptides comprising:
(a) providing a hybrid molecule, comprising a target protein and an effector within a host cell;
(b) introducing a test peptide or a population of test peptides into the host cell, wherein the peptide is linked to a carrier protein, said carrier protein being linked to a cell compartment localization domain;
(c) detection of a signal identifying the protein-peptide interaction of the hybrid molecule and the peptide; and optionally
(d) isolating a peptide, identified as a binding partner based on its ability to alter the signal when present.

For details of appropriate host cells, target protein, effectors, peptides, carrier proteins, compartment localization domains as well as a detectable signal see supra and the examples. Beside peptides (JIP20, A3Gaa122-141 and A3Gaa50-69), which are exemplified in the examples, the present invention also employs peptides and population of peptides being encoded by a nucleic acid library, for example a cDNA or EST library. It is known that peptide-encoding DNA-libraries can be designed based on information about binding preferences of the target protein. Therefore, in order to find novel candidates of interacting peptides or to identify peptides with an improved affinity to the target protein, keeping certain amino acids of the library peptides at constant positions is suggestive, since some amino acids could represent an important part of a binding motif, which may already be known. Different examples for the use of biased peptide libraries have been described in the literature; see for example Pero et al., Int. J. Cancer: 111 (2004), 951-960; Rajagopal et al., Bioorg. Med. Chem. Letters 14 (2004), 1389-1393; O'Boyle et al., Virology 236 (1997), 338-347; Linn et al., J. Biol. Chem. 378 (1997), 531.

Furthermore, populations of peptides can be enriched for peptides with, for example, a desired property such as hydrophobicity, net charge, polarity or side chain size. Methods for quantitative codon optimization of respective DNA libraries are incorporated herein by reference; see for example Larsson et al, Nucleic Acids Res. 30: e133 (2002); Park et al., Computers Chem. Engineering 29 (2005), 407-421.

Moreover, DNA-libraries deriving from the genome of specified organisms can also be used to encode peptide populations. Methods for generating peptide libraries using genomic DNAs from different species have been described in the literature; see Huang and Gao, Mol Biotechnology 30 (2005), 135-142. Furthermore, methods for constructing expression libraries deriving from micro-organisms and eukaryotes containing compact genomes are described in, for example, international application WO2004/074479.

As already indicated in the preceding sections, the method of the present invention can also be used in the reverse, i.e. identifying a desired target protein. In this embodiment, the peptide(s) will preferably be pre-determined. For example, peptide-ligands may be used, which are known to interact with a family of GPCRs but for which a further member is postulated and remained to be identified. With the help of the method of the present invention it shall be possible to identify and isolate such further and eventually more specific GPCRs. Thus, in yet another embodiment the present invention relates to a method for isolating a protein comprising:
(a) providing a host cell comprising a test protein or a population of test proteins and an effector, or introducing the effector;
(b) introducing the linkage of the effector to the test protein or population of test proteins;
(c) providing or introducing a peptide or population of peptides within/into the host cell, wherein the peptide is linked to a carrier protein, said carrier protein being linked to a cell compartment localisation domain;
(d) detection of a signal identifying the protein-peptide interaction; and
(e) isolating the protein identified as a binding partner based on its ability to alter the signal when present There are several ways of how the linkage in step (b) i.e. linkage of the effector to the test protein or population of test proteins can be performed, for instance, by tagging the protein and effector, respectively, with for example molecules, which are known to exhibit strong binding affinity to each other such as biotin and streptavidin, antigen and antibody or substrate and enzyme. For example, a test protein may be tagged with biotin and the effector desired to be linked to the protein is tagged with streptavidin, resulting in a corresponding biotin-streptavidin binding by which protein and effector are linked.

The tagging of protein and effector may be either performed extracellular, wherein after being tagged protein and effector are replaced both in the cell. This may be either at the same time, or they may be separately tagged and provided consecutively in the cell, i.e. the protein (which was tagged before) may be provided within the cell and the (also tagged) effector will be added later. Furthermore, protein and effector may be tagged intracellularly, by, for example, directing the tag itself to protein and/or effector provided within the cell.

For example, a protein having a known amino acid sequence may be tagged by using a tag having a complementary region with which it binds to the respective sequence or parts thereof to precisely and specifically tag said protein. Of course, the effector may be tagged accordingly if it and its sequence, respectively, is known. Once, protein or effector is tagged, the binding partner, having the respective "counterpart"-tag may be administered to allow interaction of the tags and therefore linkage of effector and protein.

The cell based systems described in the above examples may also be used to identify agonists or antagonists, simply by adding to a known pair of interacting proteins (in the above described system) a candidate agonist or antagonist interactor and assaying for an increase or decrease (respectively) in reporter gene expression, as compared to a control reaction lacking the candidate compound or protein. Particular examples of interacting proteins for which antagonists or agonists may be identified include, but are not limited to, the IL-6 receptor-ligand pair, TGF-ss receptor-ligand pair, IL-1 receptor-ligand pair and other receptor-ligand interactions, protein kinase-substrate pairs, interacting pairs of transcription factors, interacting components of signal transduction pathways (for example, cytoplasmic domains of certain receptors and G-proteins), pairs of interacting proteins involved in cell cycle regulation and neurotransmitter pairs.

Hence, the present invention also relates to a method for identifying and optionally isolating an antagonist or agonist molecule comprising:
(a) providing or introducing within/into the host cell
  (i) interacting proteins within/into a host cell partially/some of which comprising hybrid molecules, which comprise a target protein and an effector;
  (ii) a candidate agonist or antagonist molecule;
  (iii) a peptide or a population of peptides, wherein the peptide is linked to a carrier protein, said carrier protein being linked to a cell compartment localization domain
(b) detecting
  (i) a signal identifying the protein-peptide interaction of the hybrid molecule and the peptide; and optionally
  (ii) the alteration of the signal based on the ability of an agonist molecule to increase production of the signal or the ability of the antagonist to decrease production of the signal; and optionally
(c) isolating the agonist or antagonist molecule.

To facilitate large scale screening, candidate target proteins or candidate agonist or antagonists may be initially tested in pools, for example, of ten or twenty candidate compounds or protein. From pools demonstrating a positive result, the particular interacting protein or agonist or antagonist is then identified by individually assaying the components of the pool. Such systems are amenable to robotic automation or to the production of kits. Kits including the component of any of the interaction assay described herein are also included in the invention. The components (e.g., the various fusion proteins or DNA therefor) of any of the in vivo or in vitro systems of the invention may be provided sequentially or simultaneously depending on the desired experimental design.

The assay system of the present invention can also be used to test affinity reagents for protein purification. Peptides or protein domains can be identified that interact with the known membrane protein of interest and these may then be used in a purification protocol for the known protein.

In a further aspect, the present invention also relates to the peptides and proteins obtainable by the methods of the present invention as well as to the agonists and antagonists so identified. A subject peptide may be considered as a peptide of the present invention and encompassed in the scope of the claims at least as long as the subject peptide or a peptide with the corresponding amino acid sequence of natural amino acids encodable by a nucleic acid is identifiable as an interaction partner of its target protein by any one of the methods of the present invention described herein. This holds particular true if the subject peptide could not have been identified or obtained with a method hitherto available. Furthermore, later derivatizations of the peptide such as amidation, acetylation, introduction of D-amino acids, etc., well known in the art cannot change the essential feature of the subject peptide as being obtained or obtainable in kind.

In one particular embodiment the peptide essentially consists of the amino acid sequence depicted in SEQ ID NO: 6, SEQ ID NO: 8 or SEQ ID NO: 10. Naturally, the present invention also relates to the nucleic acid molecules encoding the aforementioned peptides, proteins, agonists and antagonists. Additionally, agonists or antagonists can be expressed from a separate expression system to modulate the present system of invention. These agonists or antagonists can be encoded by nucleic acid molecules or supplied as compounds.

The present invention also provides a kit for performing the method and assay of the present invention. Such a kit comprises the essential components such as for the target protein and peptide or collection of peptides, preferably in the form of a corresponding first and second expressible nucleic acid molecule, respectively, see also supra and the examples. In general, the expressible nucleic acid molecules are present in an expression vector suitable for the particular cells in which the interaction assay is performed. Appropriate expression vectors can be, for example, yeast expression vectors or mammalian cell expression vectors, depending on the cells in which the protein recruitment system is to be practiced. Each of the first and second expressible nucleic acid molecules generally contains a cloning site such as a multiple cloning site, which permits a convenient means to insert a nucleic acid molecule encoding a target protein or a peptide(s), respectively. In particular, the cloning site permits insertion of a nucleic acid such that the encoded protein is in frame with the effector protein and optionally with the linker in-between or with the carrier protein and cell compartment localization signal, respectively, which can constitute the N-terminus or the C-terminus of an encoded fusion protein. In addition, the expressible nucleic acids can contain appropriate transcription or translation start or stop signals or the like.

If desired, such a kit can contain reagents, for example, that result in optimal transfection efficiency of the nucleic acids for the particular host cell type. In addition, appropriate host cells can be included in a kit, although such cells generally are available or can be selected for a particular embodiment of the interaction assay system. Preferably, the kit of the present invention contains reagents such as those described hereinbefore useful for conducting any of the above-described methods of the present invention, comprising medium or media components, reference samples, micro arrays, culture vessels, cell suspending media, vectors, proteins, peptides, or the like. Such a kit would typically comprise a compartmentalized carrier suitable to hold in close confinement at least one container and the compounds of the kit may be sterile, where appropriate. The kit may further include a transfer means, such as pipets, for transferring any fluent component. A further possibility includes the direct transfer of the kit components to solid media, like agar containing media by mechanical transfer devices, like streaking or gridding tools.

In one particular embodiment, the kit of the present invention comprises:
(a) a cell or a culture comprising cells as defined above;
(b) a first nucleic acid vector for inserting a DNA sequence encoding a fusion protein which comprises a target protein and an effector as described supra;
(c) a second nucleic acid vector, for inserting a DNA sequence encoding a peptide and a carrier protein as defined hereinbefore;

(d) reagents and devices for transfecting the cells with the first and the second nucleic acid, and
(e) a monitoring arrangement for monitoring the signal due to protein-peptide interaction as defined supra.

The kit's carrier could further comprise reagents useful for performing said methods and may also contain means for detection. Instructions can be provided to detail the use of the components of the kit, such as written instructions, video presentations, or instructions in a format that can be opened on a computer (e.g. a diskette or CD-ROM disk). These instructions indicate, for example, how to use the method to screen for candidate peptides.

The present invention further relates to the use of the aforementioned individual components such as target proteins, carrier proteins, peptides and their encoding nucleic acid sequences, host cells, etc. in any one of the methods of the present invention. Preferably, the DNA encoding the peptide used in the methods of the present invention is randomly generated or (intentionally) designed.

It will be apparent that the methods of the present invention, the peptides obtained thereby, as well as the uses as substantially described herein or illustrated in the description and the examples, are also subject of the present invention and claimed herewith. In this respect, it is also understood that the embodiments as described in any one of the examples, can be independently used and combined with any one of the embodiments described hereinbefore and claimed in the appended claims set.

These and other embodiments are disclosed and encompassed by the description and examples of the present invention. Further literature concerning any one of the materials, methods, uses and compounds to be employed in accordance with the present invention may be retrieved from public libraries and databases, using for example electronic devices. For example the public database "Medline" may be utilized, which is hosted by the National Center for Biotechnology Information and/or the National Library of Medicine at the National Institutes of Health. Further databases and web addresses, such as those of the European Bioinformatics Institute (EBI), which is part of the European Molecular Biology Laboratory (EMBL) are known to the person skilled in the art and can also be obtained using interne search engines. An overview of patent information in biotechnology and a survey of relevant sources of patent information useful for retrospective searching and for current awareness is given in Berks, TIBTECH 12 (1994), 352-364.

The above disclosure generally describes the present invention. Several documents are cited throughout the text of this specification. Full bibliographic citations may be found at the end of the specification immediately preceding the claims. The contents of all cited references (including literature references, issued patents, published patent applications as cited throughout this application and manufacturer's specifications, instructions, etc) are hereby expressly incorporated by reference; however, there is no admission that any document cited is indeed prior art as to the present invention.

The above disclosure generally describes the present invention. A more complete under-standing can be obtained by reference to the following specific examples which are provided herein for purposes of illustration only and are not intended to limit the scope of the invention.

EXAMPLES

The examples which follow further illustrate the invention, but should not be construed to limit the scope of the invention in any way. Detailed descriptions of conventional methods, such as those employed herein can be found in the cited literature; see also "The Merck Manual of Diagnosis and Therapy" Seventeenth Ed. ed. by Beers and Berkow (Merck & Co., Inc. 2003).

The practice of the present invention will employ, unless otherwise indicated, conventional techniques of cell biology, cell culture, molecular biology, transgenic biology, microbiology, recombinant DNA, and immunology, which are within the skill of the art.

Methods in molecular genetics and genetic engineering are described generally in the current editions of Molecular Cloning: A Laboratory Manual, (Sambrook et al., (1989) Molecular Cloning: A Laboratory Manual, 2nd ed., Cold Spring Harbor Laboratory Press); DNA Cloning, Volumes I and II (Glover ed., 1985); Oligonucleotide Synthesis (Gait ed., 1984); Nucleic Acid Hybridization (Hames and Higgins eds. 1984); Transcription And Translation (Hames and Higgins eds. 1984); Culture Of Animal Cells (Freshney and Alan, Liss, Inc., 1987); Gene Transfer Vectors for Mammalian Cells (Miller and Calos, eds.); Current Protocols in Molecular Biology and Short Protocols in Molecular Biology, 3rd Edition (Ausubel et al., eds.); and Recombinant DNA Methodology (Wu, ed., Academic Press). Gene Transfer Vectors For Mammalian Cells (Miller and Calos, eds., 1987, Cold Spring Harbor Laboratory); Methods In Enzymology, Vols. 154 and 155 (Wu et al., eds.); Immobilized Cells And Enzymes (IRL Press, 1986); Perbal, A Practical Guide To Molecular Cloning (1984); the treatise, Methods In Enzymology (Academic Press, Inc., N.Y.); Immunochemical Methods In Cell And Molecular Biology (Mayer and Walker, eds., Academic Press, London, 1987); Handbook Of Experimental Immunology, Volumes I-IV (Weir and Blackwell, eds., 1986). Reagents, cloning vectors, and kits for genetic manipulation referred to in this disclosure are available from commercial vendors such as BioRad, Stratagene, Invitrogen, and Clontech. General techniques in cell culture and media collection are outlined in Large Scale Mammalian Cell Culture (Hu et al., Curr. Opin. Biotechnol. 8 (1997), 148); Serum-free Media (Kitano, Biotechnology 17 (1991), 73); Large Scale Mammalian Cell Culture (Curr. Opin. Biotechnol. 2 (1991), 375); and Suspension Culture of Mammalian Cells (Birch et al., Bioprocess Technol. 19 (1990), 251); Extracting information from cDNA arrays, Herzel et al., CHAOS 11, (2001), 98-107.

Example 1

Detection of Interaction Between JNK and TI-JIP

JNKs (c-jun N-terminal kinase) are important regulators of physiological and pathological processes. This subfamily of MAPKs (mitogen activated protein kinases) is involved in the development of various diseases including cancer, neurodegenerative diseases, cardio-vascular diseases, inflammatory diseases and diabetes. In response to membrane receptor activation the kinases can phosphorylate serin, threonine, or tyrosine residues of different substrates and thereby transfer signals from the cell surface to the nucleus. JNKs themselves get activated by the phosphorylation at threonine 183 and tyrosine 185. Analysis of interaction of JNK1 (NM 002750, Aa 1-351) with peptides is of major interest for the development of peptide-derived specific inhibitors.

This example demonstrates that the present invention can be used for the detection of molecular interactions between JNK and selected peptides. Therefore, "bait" proteins were cloned into an appropriate vector for expression of heterologous proteins in yeast (pADRS RRSmut, modified from pRS vector Sikorski and Hieter, Genetics 122 (1989), 19-27) as a fusion protein with constitutive active human Ras (hRasΔ61) which is devoid of its membrane localization signal (ΔCAAX). Polymerase chain reaction (PCR) was used to generate different JNK fragments JNK APF (T$^{183}$-A, Y$^{185}$-P) INK K55A (K$^{55}$-A) and JNKwt. Following HindIII and SmaI restriction digests fragments were cloned into restriction sites to express amino terminal Ras fusion proteins. JNK APF is a dominant negative mutant with mutations in the phosphorylation sites. JNK K55A is a functional mutant which is not able to bind ATP. Interactions with the peptide JIP20 GPGD-TYRPKRPTTLNLFPQVPRSG (SEQ ID NO: 6) were tested for the different JNKs. Peptides with similar amino acid sequences have already been shown to interact with JNK using alternative experimental methods; see for example Barr et al., J. Mol. Biol. 277 (13) (2002), 10987-10997, Barr et al., J. Mol. Biol. 279 (41) (2004), 42178-42189).

The second plasmid (see FIG. 5), which contains the URA3 gene was constructed from the pYes2 plasmid (Invitrogen) by insertion of a nucleic acid, encoding a Src myristoylation signal ("m") for membrane localization and a thioredoxin (trx) expressing cDNA (M26133) to express peptides as loop in the RsrII site or as a linear peptide at the C-terminus. Thioredoxin presents JIP20 as loop by cloning it into the RsrII site of thioredoxin. The fragment encoding JIP20 was produced by annealing of primer JIP20fRSR115 5' gtc cgg ggg aca cgt acc ggc cca age ggc cca cca cgc tca acc tct ttc cgc agg tgc cgc gga gcg 3' (SEQ ID NO: 15) and primer JIP20rRSRII 5' gac cgc tcc gcg gca cct gcg gaa aga ggt tga gcg tgg tgg gcc gct tgg gcc ggt acg tgt ccc ccg 3' (SEQ ID NO: 16). A restriction digest and cloning into the RsrII of thioredoxin was followed to allow a presentation of JIP20 as a loop.

The expression of the whole fusion protein is under the control of a GAL1 inducible promoter. Therefore, expression was induced by the addition of galactose to the medium (3% galactose and 2% raffinose). Glucose represses the activity of the GAL1 promoter and is therefore used in control plates to test the dependency of growth on the presence of the membrane localized peptide (specificity test); see FIG. 2.

Cdc25-2 yeast cells (MATα, ura3, lys2, Leu2, trpl cdc25-2, his3A200, ade 100, GAL+) were transformed with JNK constructs (wt, APF, K55A), empty vector (pADRS) and the pYesm-trx JIP20 construct (GAL1-myr-thioredoxin-JIP20aa/loop) by a modified high efficient transformation method according to Schiestl and Gietz, Curr. Genet. 16 (1989), 339-346. At a restrictive temperature of 30-37° C. the cdc 25-2 yeast mutant does not express a functional active endogenous Ras-protein. Protein-peptide interaction results in activation of the Ras-pathway by recruitment of the hRas-fusion protein to the plasma membrane. Under these conditions growth of yeast cells can be observed at the restrictive temperature of 37° C.

Cdc25-2 cells were plated onto glucose as well as on galactose containing -Leu-Ura selection media and growth was analyzed depending on the expression of JIP20. Plates were incubated at 37° C. and growth was observed after 5 days. As shown in FIG. 2a left part, cells expressing JNKwt, JNK APF, or JNKK55A and JIP20 stabilized in the loop grew at the restrictive temperature of 37° C. When expression of JIP20 was prevented by addition of glucose medium cells did not growth; see FIG. 2, right part.

In a control experiment cells were co-transformed with the same JNK1 constructs, but with a different Thioredoxin-JIP20 construct, lacking JIP (GAL1-myr-thioredoxin). The controls show that there is no cell growth in the absence of JIP20, demonstrating its dependency on the expression of JIP20 but not on the expression of thioredoxin alone; see FIG. 2b.

Example 2

Detection of Interaction Between Vif and Peptides

This example demonstrates the present invention to be useful for the detection of molecular interactions between recombinant HIV Vif (SEQ ID NO: 3) and selected peptides. Therefore, the NL4-3 Vif cDNA (SEQ ID NO: 2) was cloned into an appropriate vector for expression of heterologous proteins in yeast (pADRS Sos, modified from pSos vector (Sikorski and Hieter, Genetics 122 (1989), 19-27) as a fusion protein with Sos including a small spacer (SEQ ID NO: 1).

Vif cDNA was amplified by polymerase chain reaction (PCR) with primer Vif/RsrII (5' ftftCGGACCGGAAAACA-GATGGCAGGTGATG-3'; SEQ ID NO: 4) and Vif/NotI (5' aaatatGCGGCCGCCTATCTGGGGCTTGTTCCATCTG-3'; SEQ ID NO: 5). Following RsrII and NotI restriction digest Vif PCR product was cloned into equally digested pADH-Sos-2xSpc resulting in pADH-Sos-2xSpc-vif to express the amino terminal Sos fusion protein. Interactions with peptides deriving from the protein sequence of APOBEC3G were tested for the HIV-protein Vif.

The second plasmid, which contains the URA3 gene was constructed from the pYes2 plasmid (Invitrogen) by insertion of a nucleic acid containing a Src myristoylation signal ("m") for membrane localization and a thioredoxin expressing cDNA (M26133) to express peptides as a loop in the RsrII site of thioredoxin. Thioredoxin presents peptides A3Gaa122-141 (SEQ ID NO: 10), A3Gaa122-141-D128K (SEQ ID NO: 12), A3Gaa122-141scr (SEQ ID NO: 14) and A3Gaa50-69 (SEQ ID NO: 8) as loops by cloning them into the RsrII site of thioredoxin. These fragments encoding peptides were produced by annealing of two primers: A3 Gforw_aa122-141 (SEQ ID NO: 17) and A3Grev_aa122-141 (SEQ ID NO: 18) for construction of A3Gaa122-141, A3 Gforw_aa122-141-D128K (SEQ ID NO: 19) and A3Grev_aa122-141-D128K (SEQ ID NO: 20) for construction of A3Gaa122-141-D128K, A3 Gforw_aa122-141scr (SEQ ID NO: 21) and A3Grev_aa122-141scr (SEQ ID NO: 22) for construction of A3Gaa122-141scr and for the construction of A3Gaa50-69 peptide primer A3 Gforw_aa50-69 (SEQ ID NO: 23) and primer A3Grev_aa50-69 (SEQ ID NO: 24) were used.

The expression of the whole fusion protein is under the control of a GAL1 inducible promoter. Therefore, expression was induced by the addition of galactose to the medium (3% galactose and 2% raffinose). Glucose represses the activity of the GAL1 promoter and is therefore used in control plates to test the dependency of growth on the presence of the membrane localized peptide (Specificity test). No growth has been observed under glucose conditions at the restrictive temperature of 37° C.

Cdc25-2 yeast cells (MATa, ura3, lys2, Leu2, trpl cdc25-2, his3A200, ade 100, GAL+) were transformed with the pYesm-thioredoxin-peptide construct and vif construct or a control vector (pADR-Sos-2xSpc-cJun) by modified high efficient transformation method (Schiestl and Gietz, Curr. Genet. 16 (1989), 339-346). Growth of yeast cells can be observed at the restrictive temperature of 37° C.

Cdc 25-2 cells were plated onto glucose and galactose containg Leu-Ura selection media and growth was analyzed depending on the expression of peptides A3Gaa122-141 (SEQ ID NO: 10), A3Gaa122-141-D128K (SEQ ID NO: 12), A3Gaa122-141scr (SEQ ID NO: 14) and A3Gaa50-69 (SEQ ID NO: 8). Plates were incubated at 37° C. and growth was controlled after 5 days. As shown in FIG. 3 cells expressing Vif and peptides A3Gaa122-141 (SEQ ID NO: 10) or A3Gaa50-69 (SEQ ID NO: 8) stabilized in the loop grew at the restrictive temperature of 37° C. When expression of peptides was prevented by use of glucose medium cells did not grow.

Example 3

Isolation of JNK Binding Peptides from Libraries

This example demonstrates that the invention is also useful for the identification of binding sequences from peptide populations. In the following example a JNK (c-Jun N-terminal kinase) binding peptide is isolated from a sequence population containing random as well as predefined peptides.

The "bait plasmid" (pADRS-JNKAPF) was constructed as already described in Example 1. Plasmids (pYESm-thioredoxin) that express defined INK binding peptides either as loop inserted in the RsrII site of thioredoxin (as for JIP 20, Example 1) or as linear peptides at the C-terminus of thioredoxin (JIPl5aa: TYRPKRPTTLNLFPQ; SEQ ID NO: 25) and control peptides (JIP15rev: QPFLNLTTPRKPRYT; SEQ ID NO: 26 and JIP15scr: LRFQPYPKNLTPTRT; SEQ ID NO: 27) were added in defined amounts (10 ng, 100 ng) to a random DNA sequence population from Hela cells (2 µg) which is expressed from the pYesm (described in Example 1). JIP15 and control peptide sequences were generated by primer annealing and inserted into EcoRI/XhoI site in frame to the C-terminus of thioredoxin.

In comparison to the defined peptides, which are presented by a membrane localized thioredoxin, sequences from the random library also have a myristoylation signal but are not presented by the carrier. The amount of plasmid DNA expressing the peptides JIP15, JIP20, JIPrev and JIPscr varied in different approaches between 10 ng and 100 ng. The DNA mixture was co-transformed into the yeast strain cdc25-2 with 300 ng pADRS INK APF as "bait" plasmid according to the conventional transfection method as already described in Example 1. To select for "bait" and library plasmid the cells were plated on -Leu-Ura Glucose selection plate. After transferring the cells to galactose containing -Leu-Ura plate and incubation for 3-5 days at 37° C. the growth selection occurs for clones expressing JNK1 APF binding sequences from the library. Preliminary positive clones were picked and incubated in liquid -leu-ura glucose. After two days of incubation a specificity test was done, where growth is analyzed at 37° C. dependent on the expression of the library peptide (under galactose conditions). The number of positive clones varied between 66 up to 90 (for 10 ng/2 µHela DNA) and 368 up to 452 (for 100 ng/2 Hela) for JIP20 and JIP15 peptide. In all approaches the same amount (10 ng, 100 ng) of control peptides was added. To further evaluate the clones PCR was performed. Exemplary results from colony PCR of clones from a JIP20 screening are shown in FIG. 4.

A first colony PCR was done to analyze the existence of thioredoxin with the following primer: P1trxASmaIforw 5'-ccc ccc ggg atg agc gat aaa att att cac c-3' (SEQ ID NO: 28) and P2trxAEcoRIrev 5'-ttt tga att ccc gcc agg tta gcg tcg ag-3' (SEQ ID NO: 29) resulting in a 416 by fragment and in a second colony PCR the existence of JIP 20 was analyzed by using primer P3trxASmaIforw 5'-ccc ccc ggg atg agc gat aaa att att cac c-3' (SEQ ID NO: 30) and P4JipXho 5' tcg agt cac tgc gga aag agg ttg agc gtg gtg ggc-3' (SEQ ID NO: 31) resulting in a 162 by fragment. As shown in FIG. 4, yeast clones (B9, C9, D9, A4, A5, A1 and C3) were positive for the existence of the 416 by thioredoxin fragment as well as for the existence of the 162 by JIP 20 fragment. Clones B3 and F6 were also considered as positive after the growth analysis, however, a positive PCR result was not obtained. Those clones could express JNK-interacting proteins from the Hela library.

In summary, the experiments performed in accordance with the present invention demonstrate the power of the method and assay of the present invention for identifying and obtaining peptides such as peptide-ligands capable of interacting with a target protein and thus is expected to prove useful for the identification of yet unknown binding partners as well as in drug development.

The invention claimed is:

1. A method of identifying a protein-peptide interaction or isolating a partner of a protein-peptide interaction, comprising:
  (a) providing with a host cell
    (i) a hybrid molecule, comprising a target protein and an effector;
    (ii) a peptide or a population of peptides, wherein the peptide is linked to a carrier protein, said carrier protein being linked to a cell compartment localisation domain, wherein said carrier protein is selected from the group consisting of *Escherichia coli* thioredoxin, and an *Escherichia coli* thioredoxin-like molecule, and wherein said cell compartment localisation domain is a membrane localization domain, wherein said membrane localization domain is a myristoylation signal linked to the N-terminus of the *Escherichia coli* thioredoxin or *Escherichia coli* thioredoxin-like molecule; and
  (b) detection of a signal identifying the protein-peptide interaction of the hybrid molecule and the peptide; and optionally
  (c) isolating a partner of the protein-peptide interaction based on its ability to alter the signal when present.

2. The method of claim 1, wherein the carrier protein is *Escherichia coli* thioredoxin.

3. The method of claim 1, wherein the host cell lacks an active endogenous effector.

4. The method of claim 1, wherein the host cell is a yeast cell.

5. The method of claim 4, wherein the yeast cell is a *Saccharomyces cerevisiae* cdc25-2 cell.

6. The method of claim 1, wherein the host cell is selected from the group consisting of CHO, HEK, COS7, 3T3, and 293.

7. The method of claim 1, wherein the detectable signal is due to activation of a Ras-protein.

8. The method of claim 1, wherein the effector is a Sos-Protein and/or a Ras-protein lacking a farnesylation box.

9. The method of claim 1 wherein the peptide is a peptide of 10 to 30 amino acids length.

10. A method of detecting and/or isolating an interacting peptide in a population of peptides comprising:
  (a) providing a hybrid molecule comprising a target protein and an effector within a host cell;
  (b) introducing a test peptide or a population of test peptides into the host cell, wherein the peptide is linked to a carrier protein, said carrier protein being linked to a cell compartment localization domain, wherein said carrier protein is selected from the group consisting of *Escherichia coli* thioredoxin, and an *Escherichia coli* thioredoxin-like molecule, and wherein said cell compartment localization domain is a membrane localization domain, wherein said membrane localization domain is a myristoylation signal linked to the N-terminus of the *Escherichia coli*thioredoxin or *Escherichia coli* thioredoxin-like molecule; and (c) detection of a signal identifying the protein-peptide interaction of the hybrid molecule and the peptide; and optionally (d) isolating a peptide, identified as a binding partner based on its ability to alter the signal when present.

11. The method of claim 10, wherein the population of peptides is encoded by a cDNA library.

12. A method of isolating a protein comprising:

(a) providing a host cell comprising a test protein or a population of test proteins and an effector, or introducing the effector;

(b) introducing the linkage of the effector to the test protein or population of test proteins;

(c) providing or introducing a peptide or population of peptides within/into the host cell, wherein the peptide is linked to a carrier protein, said carrier protein being linked to a cell compartment localization domain, wherein said carrier protein is selected from the group consisting of *Escherichia coli* thioredoxin, and an *Escherichia coli* thioredoxin-like molecule, and wherein said cell compartment localization domain is a membrane localization domain, wherein said membrane localization domain is a myristoylation signal linked to the N-terminus of the *Escherichia coli*thioredoxin or *Escherichia coli* thioredoxin-like molecule; and (d) detection of a signal identifying the protein-peptide interaction; and (e) isolating the protein identified as a binding partner based on its ability to alter the signal when present.

* * * * *

SEQUENCE LISTING

```
<160> NUMBER OF SEQ ID NOS: 31

<210> SEQ ID NO 1
<211> LENGTH: 8
<212> TYPE: PRT
<213> ORGANISM: artificial sequence
<220> FEATURE:
<223> OTHER INFORMATION: oligopeptide

<400> SEQUENCE: 1

Gly Gly Gly Ser Gly Gly Gly Ser
1               5

<210> SEQ ID NO 2
<211> LENGTH: 624
<212> TYPE: DNA
<213> ORGANISM: Human immunodeficiency virus
<220> FEATURE:
<221> NAME/KEY: CDS
<222> LOCATION: (1)..(624)
<223> OTHER INFORMATION: ORF of HIV-Vif

<400> SEQUENCE: 2 atg gat tac aag gat gac gac gat aag agc ccg ggc gga tcc acc atg      48
Met Asp Tyr Lys Asp Asp Asp Asp Lys Ser Pro Gly Gly Ser Thr Met
1               5                   10                  15
```

| | | |
|---|---|---|
| gaa aac aga tgg cag gtg atg att gtg tgg caa gta gac agg atg agg<br>Glu Asn Arg Trp Gln Val Met Ile Val Trp Gln Val Asp Arg Met Arg<br>20 25 30 | | 96 |
| att aac aca tgg aaa aga tta gta aaa cac cat atg tat att tca agg<br>Ile Asn Thr Trp Lys Arg Leu Val Lys His His Met Tyr Ile Ser Arg<br>35 40 45 | | 144 |
| aaa gct aag gac tgg ttt tat aga cat cac tat gaa agt act aat cca<br>Lys Ala Lys Asp Trp Phe Tyr Arg His His Tyr Glu Ser Thr Asn Pro<br>50 55 60 | | 192 |
| aaa ata agt tca gaa gta cac atc cca cta ggg gat gct aaa tta gta<br>Lys Ile Ser Ser Glu Val His Ile Pro Leu Gly Asp Ala Lys Leu Val<br>65 70 75 80 | | 240 |
| ata aca aca tat tgg ggt ctg cat aca gga gaa aga gac tgg cat ttg<br>Ile Thr Thr Tyr Trp Gly Leu His Thr Gly Glu Arg Asp Trp His Leu<br>85 90 95 | | 288 |
| ggt cag gga gtc tcc ata gaa tgg agg aaa aag aga tat agc aca caa<br>Gly Gln Gly Val Ser Ile Glu Trp Arg Lys Lys Arg Tyr Ser Thr Gln<br>100 105 110 | | 336 |
| gta gac cct gac cta gca gac caa cta att cat ctg cac tat ttt gat<br>Val Asp Pro Asp Leu Ala Asp Gln Leu Ile His Leu His Tyr Phe Asp<br>115 120 125 | | 384 |
| tgt ttt tca gaa tct gct ata aga aat acc ata tta gga cgt ata gtt<br>Cys Phe Ser Glu Ser Ala Ile Arg Asn Thr Ile Leu Gly Arg Ile Val<br>130 135 140 | | 432 |
| agt cct agg tgt gaa tat caa gca gga cat aac aag gta gga tct cta<br>Ser Pro Arg Cys Glu Tyr Gln Ala Gly His Asn Lys Val Gly Ser Leu<br>145 150 155 160 | | 480 |
| cag tac ttg gca cta gca gca tta ata aaa cca aaa cag ata aag cca<br>Gln Tyr Leu Ala Leu Ala Ala Leu Ile Lys Pro Lys Gln Ile Lys Pro<br>165 170 175 | | 528 |
| cct ttg cct agt gtt agg aaa ctg aca gag gac aga tgg aac aag ccc<br>Pro Leu Pro Ser Val Arg Lys Leu Thr Glu Asp Arg Trp Asn Lys Pro<br>180 185 190 | | 576 |
| cag aag acc aag ggc cac aga ggg agc cat aca atg aat ggt cac tag<br>Gln Lys Thr Lys Gly His Arg Gly Ser His Thr Met Asn Gly His<br>195 200 205 | | 624 |

<210> SEQ ID NO 3
<211> LENGTH: 207
<212> TYPE: PRT
<213> ORGANISM: Human immunodeficiency virus

<400> SEQUENCE: 3

Met Asp Tyr Lys Asp Asp Asp Lys Ser Pro Gly Gly Ser Thr Met
1               5                   10                  15

Glu Asn Arg Trp Gln Val Met Ile Val Trp Gln Val Asp Arg Met Arg
                20                  25                  30

Ile Asn Thr Trp Lys Arg Leu Val Lys His His Met Tyr Ile Ser Arg
            35                  40                  45

Lys Ala Lys Asp Trp Phe Tyr Arg His His Tyr Glu Ser Thr Asn Pro
        50                  55                  60

Lys Ile Ser Ser Glu Val His Ile Pro Leu Gly Asp Ala Lys Leu Val
65                  70                  75                  80

Ile Thr Thr Tyr Trp Gly Leu His Thr Gly Glu Arg Asp Trp His Leu
                85                  90                  95

Gly Gln Gly Val Ser Ile Glu Trp Arg Lys Lys Arg Tyr Ser Thr Gln
            100                 105                 110

Val Asp Pro Asp Leu Ala Asp Gln Leu Ile His Leu His Tyr Phe Asp
        115                 120                 125

```
Cys Phe Ser Glu Ser Ala Ile Arg Asn Thr Ile Leu Gly Arg Ile Val
        130                 135                 140

Ser Pro Arg Cys Glu Tyr Gln Ala Gly His Asn Lys Val Gly Ser Leu
145                 150                 155                 160

Gln Tyr Leu Ala Leu Ala Ala Leu Ile Lys Pro Lys Gln Ile Lys Pro
                165                 170                 175

Pro Leu Pro Ser Val Arg Lys Leu Thr Glu Asp Arg Trp Asn Lys Pro
            180                 185                 190

Gln Lys Thr Lys Gly His Arg Gly Ser His Thr Met Asn Gly His
        195                 200                 205

<210> SEQ ID NO 4
<211> LENGTH: 32
<212> TYPE: DNA
<213> ORGANISM: artificial sequence
<220> FEATURE:
<223> OTHER INFORMATION: oligonucleotide
<220> FEATURE:
<221> NAME/KEY: misc_feature
<222> LOCATION: (1)..(32)
<223> OTHER INFORMATION: Primer Vif/RsrII

<400> SEQUENCE: 4
ttttcggacc ggaaaacaga tggcaggtga tg                                32

<210> SEQ ID NO 5
<211> LENGTH: 37
<212> TYPE: DNA
<213> ORGANISM: artificial sequence
<220> FEATURE:
<223> OTHER INFORMATION: oligonucleotide
<220> FEATURE:
<221> NAME/KEY: misc_feature
<222> LOCATION: (1)..(37)
<223> OTHER INFORMATION: Primer Vif/NotI

<400> SEQUENCE: 5
aaatatgcgg ccgcctatct ggggcttgtt ccatctg                           37

<210> SEQ ID NO 6
<211> LENGTH: 24
<212> TYPE: PRT
<213> ORGANISM: artificial sequence
<220> FEATURE:
<223> OTHER INFORMATION: oligopeptide
<220> FEATURE:
<221> NAME/KEY: PEPTIDE
<222> LOCATION: (1)..(24)
<223> OTHER INFORMATION: JIP20

<400> SEQUENCE: 6

Gly Pro Gly Asp Thr Tyr Arg Pro Lys Arg Pro Thr Thr Leu Asn Leu
1               5                   10                  15

Phe Pro Gln Val Pro Arg Ser Gly
            20

<210> SEQ ID NO 7
<211> LENGTH: 60
<212> TYPE: DNA
<213> ORGANISM: artificial sequence
<220> FEATURE:
<223> OTHER INFORMATION: oligonucleotide
<220> FEATURE:
<221> NAME/KEY: CDS
<222> LOCATION: (1)..(60)
<223> OTHER INFORMATION: DNA encoding Peptide A3Gaa50-69
```

-continued

<400> SEQUENCE: 7

| gac | gca | aag | atc | ttt | cga | ggc | cag | gtg | tat | tcc | gaa | ctt | aag | tac | cac | 48 |
| Asp | Ala | Lys | Ile | Phe | Arg | Gly | Gln | Val | Tyr | Ser | Glu | Leu | Lys | Tyr | His | |
| 1 | | | | 5 | | | | | 10 | | | | | 15 | | |

| cca | gag | atg | aga | | | | | | | | | | | | | 60 |
| Pro | Glu | Met | Arg | | | | | | | | | | | | | |
| | | | 20 | | | | | | | | | | | | | |

<210> SEQ ID NO 8
<211> LENGTH: 20
<212> TYPE: PRT
<213> ORGANISM: artificial sequence
<220> FEATURE:
<223> OTHER INFORMATION: Synthetic Construct

<400> SEQUENCE: 8

Asp Ala Lys Ile Phe Arg Gly Gln Val Tyr Ser Glu Leu Lys Tyr His
1               5                   10                  15

Pro Glu Met Arg
            20

<210> SEQ ID NO 9
<211> LENGTH: 60
<212> TYPE: DNA
<213> ORGANISM: artificial sequence
<220> FEATURE:
<223> OTHER INFORMATION: oligonucleotide
<220> FEATURE:
<221> NAME/KEY: CDS
<222> LOCATION: (1)..(60)
<223> OTHER INFORMATION: DNA encoding peptide A3Gaa122-141

<400> SEQUENCE: 9

| cgc | ctc | tac | tac | ttc | tgg | gac | cca | gat | tac | cag | gag | gct | ctt | cgc | agc | 48 |
| Arg | Leu | Tyr | Tyr | Phe | Trp | Asp | Pro | Asp | Tyr | Gln | Glu | Ala | Leu | Arg | Ser | |
| 1 | | | | 5 | | | | | 10 | | | | | 15 | | |

| ctg | tgt | cag | aaa | | | | | | | | | | | | | 60 |
| Leu | Cys | Gln | Lys | | | | | | | | | | | | | |
| | | | 20 | | | | | | | | | | | | | |

<210> SEQ ID NO 10
<211> LENGTH: 20
<212> TYPE: PRT
<213> ORGANISM: artificial sequence
<220> FEATURE:
<223> OTHER INFORMATION: Synthetic Construct

<400> SEQUENCE: 10

Arg Leu Tyr Tyr Phe Trp Asp Pro Asp Tyr Gln Glu Ala Leu Arg Ser
1               5                   10                  15

Leu Cys Gln Lys
            20

<210> SEQ ID NO 11
<211> LENGTH: 60
<212> TYPE: DNA
<213> ORGANISM: artificial sequence
<220> FEATURE:
<223> OTHER INFORMATION: oligonucleotide
<220> FEATURE:
<221> NAME/KEY: CDS
<222> LOCATION: (1)..(60)
<223> OTHER INFORMATION: DNA encoding peptide A3Gaa122-141-D128K

<400> SEQUENCE: 11

```
cgc ctc tac tac ttc tgg aag cca gat tac cag gag gct ctt cgc agc    48
Arg Leu Tyr Tyr Phe Trp Lys Pro Asp Tyr Gln Glu Ala Leu Arg Ser
 1               5                  10                  15 ctg tgt cag aaa                                                    60
Leu Cys Gln Lys
            20
```

<210> SEQ ID NO 12
<211> LENGTH: 20
<212> TYPE: PRT
<213> ORGANISM: artificial sequence
<220> FEATURE:
<223> OTHER INFORMATION: Synthetic Construct

<400> SEQUENCE: 12

```
Arg Leu Tyr Tyr Phe Trp Lys Pro Asp Tyr Gln Glu Ala Leu Arg Ser
 1               5                  10                  15

Leu Cys Gln Lys
            20
```

<210> SEQ ID NO 13
<211> LENGTH: 60
<212> TYPE: DNA
<213> ORGANISM: artificial sequence
<220> FEATURE:
<223> OTHER INFORMATION: oligonucleotide
<220> FEATURE:
<221> NAME/KEY: CDS
<222> LOCATION: (1)..(60)
<223> OTHER INFORMATION: DNA encoding peptide A3Gaa122-141scr

<400> SEQUENCE: 13

```
tac ctc cca gac agc tac tgt gct aaa tgg cag cgc cag ctg gat ttc    48
Tyr Leu Pro Asp Ser Tyr Cys Ala Lys Trp Gln Arg Gln Leu Asp Phe
 1               5                  10                  15 ctt tac cgc gag                                                    60
Leu Tyr Arg Glu
            20
```

<210> SEQ ID NO 14
<211> LENGTH: 20
<212> TYPE: PRT
<213> ORGANISM: artificial sequence
<220> FEATURE:
<223> OTHER INFORMATION: Synthetic Construct

<400> SEQUENCE: 14

```
Tyr Leu Pro Asp Ser Tyr Cys Ala Lys Trp Gln Arg Gln Leu Asp Phe
 1               5                  10                  15

Leu Tyr Arg Glu
            20
```

<210> SEQ ID NO 15
<211> LENGTH: 69
<212> TYPE: DNA
<213> ORGANISM: artificial sequence
<220> FEATURE:
<223> OTHER INFORMATION: oligonucleotide
<220> FEATURE:
<221> NAME/KEY: misc_feature
<222> LOCATION: (1)..(69)
<223> OTHER INFORMATION: Primer (JIP20fRSR115)

<400> SEQUENCE: 15

```
gtccggggga cacgtaccgg cccaagcggc ccaccacgct caacctcttt ccgcaggtgc    60
cgcggagcg                                                            69
```

```
<210> SEQ ID NO 16
<211> LENGTH: 69
<212> TYPE: DNA
<213> ORGANISM: artificial sequence
<220> FEATURE:
<223> OTHER INFORMATION: oligonucleotide
<220> FEATURE:
<221> NAME/KEY: misc_feature
<222> LOCATION: (1)..(69)
<223> OTHER INFORMATION: Primer (JIP20rRSRII)

<400> SEQUENCE: 16
gaccgctccg cggcacctgc ggaaagaggt tgagcgtggt gggccgcttg ggccggtacg    60
tgtcccccg                                                            69

<210> SEQ ID NO 17
<211> LENGTH: 69
<212> TYPE: DNA
<213> ORGANISM: artificial sequence
<220> FEATURE:
<223> OTHER INFORMATION: oligonucleotide
<220> FEATURE:
<221> NAME/KEY: misc_feature
<222> LOCATION: (1)..(69)
<223> OTHER INFORMATION: Primer A3Gforw_aa122-141

<400> SEQUENCE: 17
gtccgcgcct ctactacttc tgggacccag attaccagga ggctcttcgc agcctgtgtc    60
agaaaagcg                                                            69

<210> SEQ ID NO 18
<211> LENGTH: 69
<212> TYPE: DNA
<213> ORGANISM: artificial sequence
<220> FEATURE:
<223> OTHER INFORMATION: oligonucleotide
<220> FEATURE:
<221> NAME/KEY: misc_feature
<222> LOCATION: (1)..(69)
<223> OTHER INFORMATION: Primer A3Grev_aa122-141

<400> SEQUENCE: 18
gaccgctttt ctgacacagg ctgcgaagag cctcctggta atctgggtcc cagaagtagt    60
agaggcgcg                                                            69

<210> SEQ ID NO 19
<211> LENGTH: 69
<212> TYPE: DNA
<213> ORGANISM: artificial sequence
<220> FEATURE:
<223> OTHER INFORMATION: oligonucleotide
<220> FEATURE:
<221> NAME/KEY: misc_feature
<222> LOCATION: (1)..(69)
<223> OTHER INFORMATION: Primer A3Gforw_aa122-141-D128K

<400> SEQUENCE: 19
gtccgcgcct ctactacttc tggaagccag attaccagga ggctcttcgc agcctgtgtc    60
agaaaagcg                                                            69

<210> SEQ ID NO 20
<211> LENGTH: 69
<212> TYPE: DNA
<213> ORGANISM: artificial sequence
<220> FEATURE:
```

<223> OTHER INFORMATION: oligonucleotide
<220> FEATURE:
<221> NAME/KEY: misc_feature
<222> LOCATION: (1)..(69)
<223> OTHER INFORMATION: Primer A3Grev_aa122-141-D128K

<400> SEQUENCE: 20
gaccgctttt ctgacacagg ctgcgaagag cctcctggta atctggcttc cagaagtagt    60
agaggcgcg    69

<210> SEQ ID NO 21
<211> LENGTH: 69
<212> TYPE: DNA
<213> ORGANISM: artificial sequence
<220> FEATURE:
<223> OTHER INFORMATION: oligonucleotide
<220> FEATURE:
<221> NAME/KEY: misc_feature
<222> LOCATION: (1)..(69)
<223> OTHER INFORMATION: Primer A3Gforw_aa122-141scr

<400> SEQUENCE: 21
gtccgtacct cccagacagc tactgtgcta aatggcagcg ccagctggat ttcctttacc    60
gcgagagcg    69

<210> SEQ ID NO 22
<211> LENGTH: 69
<212> TYPE: DNA
<213> ORGANISM: artificial sequence
<220> FEATURE:
<223> OTHER INFORMATION: oligonucleotide
<220> FEATURE:
<221> NAME/KEY: misc_feature
<222> LOCATION: (1)..(69)
<223> OTHER INFORMATION: Primer A3Grev_aa122-141scr

<400> SEQUENCE: 22
gaccgctctc gcggtaaagg aaatccagct ggcgctgcca tttagcacag tagctgtctg    60
ggaggtacg    69

<210> SEQ ID NO 23
<211> LENGTH: 69
<212> TYPE: DNA
<213> ORGANISM: artificial sequence
<220> FEATURE:
<223> OTHER INFORMATION: oligonucleotide
<220> FEATURE:
<221> NAME/KEY: misc_feature
<222> LOCATION: (1)..(69)
<223> OTHER INFORMATION: Primer A3Gforw_aa50-69

<400> SEQUENCE: 23
gtccggacgc aaagatcttt cgaggccagg tgtattccga acttaagtac cacccagaga    60
tgagaagcg    69

<210> SEQ ID NO 24
<211> LENGTH: 69
<212> TYPE: DNA
<213> ORGANISM: artificial sequence
<220> FEATURE:
<223> OTHER INFORMATION: oligonucleotide
<220> FEATURE:
<221> NAME/KEY: misc_feature
<222> LOCATION: (1)..(69)
<223> OTHER INFORMATION: Primer A3Grev_aa50-69

<400> SEQUENCE: 24

```
gaccgcttct catctctggg tggtacttaa gttcggaata cacctggcct cgaaagatct    60
ttgcgtccg                                                            69
```

<210> SEQ ID NO 25
<211> LENGTH: 15
<212> TYPE: PRT
<213> ORGANISM: artificial sequence
<220> FEATURE:
<223> OTHER INFORMATION: oligopeptide
<220> FEATURE:
<221> NAME/KEY: PEPTIDE
<222> LOCATION: (1)..(15)
<223> OTHER INFORMATION: JIP 15aa
<220> FEATURE:
<221> NAME/KEY: PEPTIDE
<222> LOCATION: (1)..(15)
<223> OTHER INFORMATION: JIP15aa

<400> SEQUENCE: 25

```
Thr Tyr Arg Pro Lys Arg Pro Thr Thr Leu Asn Leu Phe Pro Gln
1               5                   10                  15
```

<210> SEQ ID NO 26
<211> LENGTH: 15
<212> TYPE: PRT
<213> ORGANISM: artificial sequence
<220> FEATURE:
<223> OTHER INFORMATION: oligopeptide
<220> FEATURE:
<221> NAME/KEY: PEPTIDE
<222> LOCATION: (1)..(15)
<223> OTHER INFORMATION: JIP15rev

<400> SEQUENCE: 26

```
Gln Pro Phe Leu Asn Leu Thr Thr Pro Arg Lys Pro Arg Tyr Thr
1               5                   10                  15
```

<210> SEQ ID NO 27
<211> LENGTH: 15
<212> TYPE: PRT
<213> ORGANISM: artificial sequence
<220> FEATURE:
<223> OTHER INFORMATION: oligopeptide
<220> FEATURE:
<221> NAME/KEY: PEPTIDE
<222> LOCATION: (1)..(15)
<223> OTHER INFORMATION: JIP15scr

<400> SEQUENCE: 27

```
Leu Arg Phe Gln Pro Tyr Pro Lys Asn Leu Thr Pro Thr Arg Thr
1               5                   10                  15
```

<210> SEQ ID NO 28
<211> LENGTH: 31
<212> TYPE: DNA
<213> ORGANISM: artificial sequence
<220> FEATURE:
<223> OTHER INFORMATION: oligonucleotide
<220> FEATURE:
<221> NAME/KEY: misc_feature
<222> LOCATION: (1)..(31)
<223> OTHER INFORMATION: Primer (P1trxASmaIforw)

<400> SEQUENCE: 28

```
cccccccggga tgagcgataa aattattcac c                                  31
```

<210> SEQ ID NO 29
<211> LENGTH: 29

```
<212> TYPE: DNA
<213> ORGANISM: artificial sequence
<220> FEATURE:
<223> OTHER INFORMATION: oligonucleotide
<220> FEATURE:
<221> NAME/KEY: misc_feature
<222> LOCATION: (1)..(29)
<223> OTHER INFORMATION: Primer (P2trxAEcoRIrev)

<400> SEQUENCE: 29
ttttgaattc cgccaggtt agcgtcgag                                    29

<210> SEQ ID NO 30
<211> LENGTH: 31
<212> TYPE: DNA
<213> ORGANISM: artificial sequence
<220> FEATURE:
<223> OTHER INFORMATION: oligonucleotide
<220> FEATURE:
<221> NAME/KEY: misc_feature
<222> LOCATION: (1)..(31)
<223> OTHER INFORMATION: Primer (P3trxASmaIforw)

<400> SEQUENCE: 30 cccccggga tgagcgataa aattattcac c                                 31

<210> SEQ ID NO 31
<211> LENGTH: 36
<212> TYPE: DNA
<213> ORGANISM: artificial sequence
<220> FEATURE:
<223> OTHER INFORMATION: oligonucleotide
<220> FEATURE:
<221> NAME/KEY: misc_feature
<222> LOCATION: (1)..(36)
<223> OTHER INFORMATION: Primer (P4JipXho)

<400> SEQUENCE: 31
tcgagtcact gcggaaagag gttgagcgtg gtgggc                           36
```